(12) United States Patent
Somers et al.

(10) Patent No.: US 8,772,225 B2
(45) Date of Patent: Jul. 8, 2014

(54) BIOMARKERS FOR MULTIPLE SCLEROSIS

(75) Inventors: Veerle Somers, Sint-Truiden (BE); Pieter Stinissen, Diepenbeek (BE)

(73) Assignee: Universiteit Hasselt, Diepenbeck (BE)

( * ) Notice: Subject to any disclaimer, the term of this patent is extended or adjusted under 35 U.S.C. 154(b) by 1303 days.

(21) Appl. No.: 12/595,597

(22) PCT Filed: Apr. 14, 2008

(86) PCT No.: PCT/EP2008/054479
§ 371 (c)(1),
(2), (4) Date: Apr. 14, 2010

(87) PCT Pub. No.: WO2008/125651
PCT Pub. Date: Oct. 23, 2008

(65) Prior Publication Data
US 2010/0297678 A1 Nov. 25, 2010

(30) Foreign Application Priority Data
Apr. 12, 2007 (EP) .................................... 07106081

(51) Int. Cl.
*A61K 31/00* (2006.01)
*A61K 38/00* (2006.01)
*A61K 38/10* (2006.01)
*A61K 38/16* (2006.01)
*C07K 7/00* (2006.01)
*C07K 14/00* (2006.01)
*C07K 17/00* (2006.01)

(52) U.S. Cl.
USPC ............ 514/1; 514/17.7; 514/17.9; 514/21.2; 514/21.5; 530/300; 530/350

(58) Field of Classification Search
None
See application file for complete search history.

(56) References Cited

U.S. PATENT DOCUMENTS

2004/0043431 A1   3/2004   Vojdani

FOREIGN PATENT DOCUMENTS

| WO | WO-03/000733 | 1/2003 |
| WO | WO-03/042701 | 5/2003 |
| WO | WO-2004/034031 | 4/2004 |

OTHER PUBLICATIONS

O'Connor et al., Disease Markers, vol. 22, pp. 213-225, 2006.*
Almeras et al., "New Antigenic Candidates in Multiple Sclerosis: Identification by Serological Proteome Analysis," *Proteomics*, 4:2184-2194 (2004).
Archelos et al., "Isolation and Characterization of an Oligodendrocyte Precursor-Derived B-Cell Epitope in Multiple Sclerosis," *Ann. Neurol.*, 43:15-24 (1998).
Baranzini et al., "B Cell Repertoire Diversity and Clonal Expansion in Multiple Sclerosis Brain Lesions," *J. Immunol.*, 163:5133-5144 (1999).
Becker et al., "Analysis of a Sequenced cDNA Library from Multiple Sclerosis Lesions," *J. Neuroirnmunol.*, 17:27-38 (1997).
Cepok et al., "Identification of Epstein-Barr Virus Proteins as Putative Targets of the Immune Response in Multiple Sclerosis," *J. Clin. Invest.*, 115:1352-1360 (2005).
Cortese et al., "CSF-Enriched Antibodies Do Not Share Specificities Among MS Patients," *Mult. Scler.*, 4:118-123 (1998).
Cortese et al., "Identification of Peptides Specific for Cerebrospinal Fluid Antibodies in Multiple Sclerosis by using Phage Libraries," *Proc. Nat. Acad. Sci.* (USA), 93:11063-11067 (1996).
Cross et al., "B Cells and Antibodies in CNS Demyelinating Disease," *J. Neuroimmunol.*, 112:1-14 (2001).
Genain et al., "Identification of Autoantibodies Associated with Myelin Damage in Multiple Sclerosis," *Nat. Med.*, 2:170-175 (1999).
Karni et al., "Elevated Levels of Antibody to Myelin Oligodendrocyte Glycoprotein is not Specific for Patients with Multiple Sclerosis," *Arch. Neurol.*, 56:311-315 (1999).
Keegan at al , "Relation Between Humoral Pathological Changes in Multiple Sclerosis and Response to Therapeutic Plasma Exchange," *Lancet*, 366:579-582 (2005).
Kollin et al., "Triosephosphate Isomerase- and Glyceraldehyde-3-Phosphate Dehydrogenase-Reactive Autoantibodies in the Cerebrospinal Fluid of Patients with Multiple Sclerosis," *J. Immunol.*, 177:5652-5658 (2006).
Lalive et al., "Antibodies to Native Myelin Oligodendrocyte Glycoprotein are Serologic Markers of Early Inflammation in Multiple Sclerosis," *Proc. Natl. Acad. Sci.* (USA), 103:2280-2285 (2006).
Larsen et al., "Improved Method for Predicting Linear B-Cell Epitopes," *Immunome. Res.*, 2:2 (2006).
Lucchinetti et al., "Distinct Patterns of Multiple Sclerosis Pathology Indicates Heterogeneity on Pathogenesis," *Brain Pathol.*, 6:259-274 (1996).
Lucchinet et al., "Heterogeneity of Multiple Sclerosis Lesons: Implications or he Pathogenesis of Demyelination," *Ann. Neurol.*, 47:707-717 (2000).
Marks et al., "By-Passing Immunization. Human Antibodies from V-Gene Libraries Displayed oh Phage," *J. Mol. Biol.*, 222:581-597 (1991).
Moller et al., "Antibodies to Myelin-Associated Glycoprotein (MAG) in the Cerebrospinal Fluid of Multiple Sclerosis Patients," *J. Neuroimmunol.*, 22:55-61 (1989).
Neer et al., "The Ancient Regulatory-Protein Family of WD-Repeat Proteins," *Nature*, 371:297-300 (1994).

(Continued)

*Primary Examiner* — Jeffrey Strucker
*Assistant Examiner* — Stephen Gucker
(74) *Attorney, Agent, or Firm* — TraskBritt, P.C.

(57) ABSTRACT

The present invention relates to the diagnosis of neurological disorders, more specifically to the diagnosis of multiple sclerosis. A biomarker panel is provided which can be used to detect if a subject has multiple sclerosis. Also described are methods of identification of such biomarkers.

10 Claims, 4 Drawing Sheets

(56) References Cited

OTHER PUBLICATIONS

Figure 1:
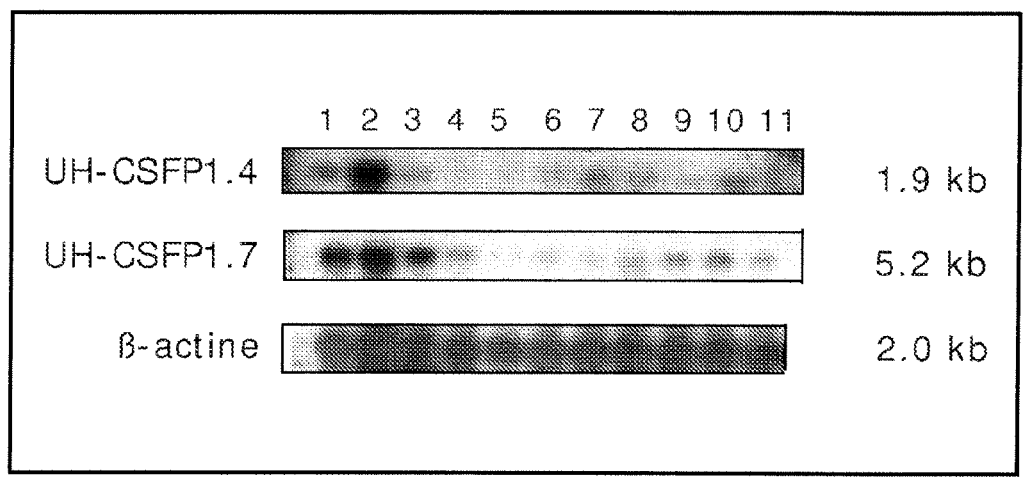

Ng et al., "Increased Noncanonical Splicing of Autoantigen Transcripts Provideds the Structural Basis for Expression of Untolerized Epitopes," *J. Allergy Clin. Immunol.*, 114:1463-1470 (2004).

O'Connor et al., "Myelin Basic Protein-Reactive Autoantibodies in the Serum and Cerebrospinal Fluid of Multiple Sclerosis Patients are Characterized by Low-Affinity Interactions," *J. Neuroimmunol.*, 136:140-148 (2003).

Ota et al., "Complete Squencing and Characterization of 21,243 Full-length Human cDNAs," *Nat. Genet.*, 36:40-45 (2004).

Owens et al., "Strategies to Identify Sequences or Antigens Unique to Multiple Sclerosis," *Mult. Scler.*, 2:184-194 (1996).

Poser et al., "New Diagnostic Criteria for Multiple Sclerosis: Guidelines for Research Protocols," *Ann. Neurol.*, 13:227-231 (1983).

Qin et al., "Clonal Expansion and Somatic Hypermutation of V(H) Genes of B Cells from Cerebrospinal Fluid in Multiple Sclerosis," *J. Clin. Invest.*, 102:1045-1050 (1998).

Robinson et al. "Protein Microarrays Guide Tolerizing DNA Vaccine Treatment of Autoimmune Encephalomyelitis," *Nat. Biotechnol.*, 21:1033-1039 (2003).

Smith et al., "PF20 Gene Product Contains WD Repeats and Localizes to the Intermicrotubule Bridges in Chlamydomonas Flagella," *Mol. Biol. Cell.*, 8:455-467 (1997).

Smith et al., "The WD Repeat: A Common Architecture of Diverse Functions," *Trends Biochem. Sci.*, 24:181-185 (1999).

Somers et al., "A Panel of Candidate Tumor Antigens in Colorectal Cancer Revealed by the Serological Selection of a Phage Displayed cDNA Expression Library," *J. Immunol.*, 169:2772-2780 (2002).

Somers et al., "Profiling the Autoantibody Repertoire by Serological Antigen Selection," *J. Autoimmun.*, 25:223-228 (2005).

Strausberg et al., "Generation and Initial Analysis of More than 15,000 Full-length Human and Mouse cDNA Sequences," *Proc. Nat. Acad. Sci.* (USA), 99:16899-16903 (2002).

Stuve et al., "Clinical Stabilization and Effective B-Lymphocyte Depletion in the Cerebrospinal Fluid and Peripheral Blood of a Patient with Fulminant Relapsing-Remitting Multiple Sclerosis," *Arch. Neurol.*, 62:1620-1623 (2005).

Towbin et al., "Electrophoretic Transfer of Proteins from Polyacrylamide Gels to Nitrocellulose Sheets: Procedure and Some Applications," *Proc. Nat. Acad. Sci.* (USA), 76:4350-4354 (1979).

Vojdani et al., "Antibodies to Myelin Basic Protein, Myelin Oligodendrocytes Peptides, Alpha-beta-Crystallin, Lymphoctye Activation and Cytokine Production in Patients with Multiple Sclerosis," *J. Intern. Med.*, 254:363-374 (2003).

Wang et al., "Autoantibody Signatures in Prostate Cancer," *N. Engl. J. Med.*, 353:1224-1235 (2005).

Yeo et al., "Variation in Alternative Splicing Across Human Tissues," *Genome Biol.*, 5:R74 (2004).

International Search Report for Application No. PCT/EP2008/054479, dated Jan. 19, 2009.

\* cited by examiner

BIOMARKERS FOR MULTIPLE SCLEROSIS

This application is the U.S. National Stage of International Application No. PCT/EP2008/054479, incorporated by reference, filed Apr. 14, 2008, which claims priority benefit of European Patent Application No. 07106081.8, filed Apr. 12, 2007.

FIELD OF THE INVENTION

The present invention relates to the diagnosis of neurological disorders, more specifically to the diagnosis of multiple sclerosis. A biomarker panel is provided which can be used to detect if a subject has multiple sclerosis. Also described are methods of identification of such biomarkers.

BACKGROUND TO THE INVENTION

Multiple sclerosis (MS) affects more than 350.000 people in the US and 2.5 million worldwide. In the US prevalence estimates vary between 5 and 119 per 100.000 and healthcare costs are estimated to be more than $10 billion annually in the US alone. It is the most common neurological disease in young adults, with the risk of subsequent chronic functional impairment and disability after 10-15% of disease duration. The disease is characterized initially in 80-90% of patients by recurrent neurological events (relapses) that are attributable to multifocal lesions within the CNS. Further disease courses vary from benign to classical relapsing-remitting (RR), primary (PP) and secondary (SP) chronic progressive or rare fulminant disease course. MS is considered to be of autoimmune origin and is characterized neuropathologically by variable extents of focal inflammation, demyelination, axonal damage, gliotic scarring and atrophy, but also by remyelination and regeneration in the CNS. This has led, together with the clinical variability, to the concept of MS as a heterogenous disease with respect to four pathogenetic mechanisms of demyelination[1,2]. One of these pathogenetic subtypes is characterized neuropathologically by antibody-dependent immune mechanisms involved in the formation of MS lesions[1,3].

During the past years, an important role of autoreactive B cells and autoantibodies has been demonstrated[4]. Recent studies uniformly showed clonal expansion of antibody-secreting B cells in the CNS and cerebrospinal fluid (CSF) of patients with MS[5,6]. Furthermore, detection of oligoclonal antibodies in CSF of patients with neurological diseases has been associated with the presence of MS. Numerous studies have reported the recognition of central nervous system (CNS) myelin autoantigens such as myelin basic protein (MBP), proteolipid lipoprotein, myelin oligodendrocyte glycoprotein, myelin associated glycoprotein by autoantibodies present in CSF and serum of MS patients, but also in patients with other-inflammatory neurological diseases (OIND) and non-inflammatory neurological diseases (NIND) as well as healthy controls[7-11].

A physician may diagnose MS in some patients soon after the onset of the illness. In others, however, doctors may not be able to readily identify the cause of the symptoms, leading to years of uncertainty and multiple diagnoses. The vast majority of patients are mildly affected, but in the worst cases, MS can render a person unable to write, speak or walk. Unfortunately, no single laboratory test is yet available to prove or rule out MS. Therefore, there is a great need in the art for improved diagnostic tests for MS. The development of a panel of biomarkers, specific for different pathophysiological mechanisms, will be crucial for the further understanding of the pathogenesis of MS, as well as diagnosis, classification, disease activity, and theranostic applications.

In the present invention, we report the identification of autoantibody binding peptides/proteins which are highly specific for MS patients. The results obtained were also correlated to disease duration, disability and different clinical course of disease. The autoantibody profiles against these selected peptides can be used as a biomarker panel for the specific detection of MS.

FIGURES

FIG. 1: Expression profile of novel antigenic targets in normal tissues. Expression patterns are shown for UH-CSF1.4 and UH-CSFP1.7. The lower panel shows a control hybridization with an actin probe. Lane 1: brain; lane 2: heart; lane 3: skeletal muscle; lane 4: colon; lane 5: thymus; lane 6: spleen; lane 7: kidney; lane 8: liver; lane 9: small intestine; lane 10: placenta; lane 11: lung; lane 12: peripheral blood lymphocytes.

Figure 2:
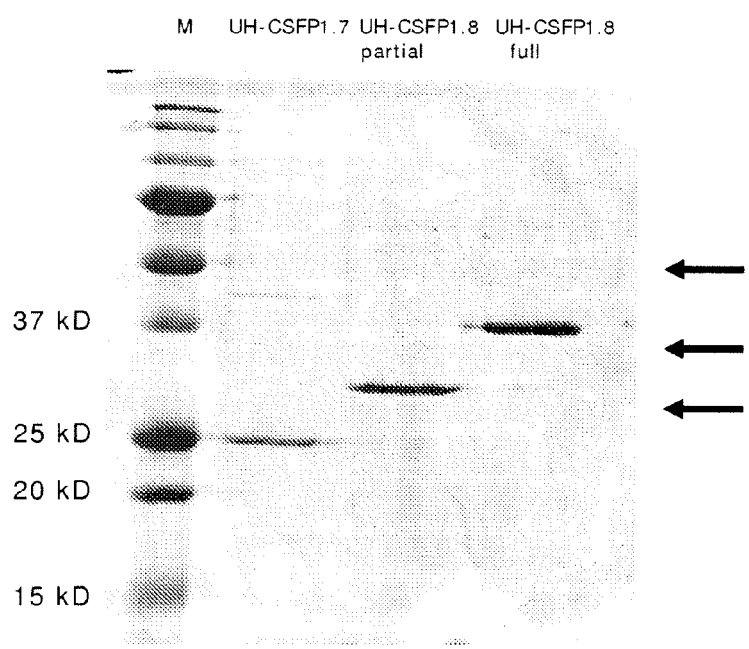

FIG. 2: UH-CSFP1.7 and UH-CSFP1.8 protein expression in E. coli. UH-CSFP1.7 was cloned as antigen (6.1 kDa) and the UH-CSFP1.8 protein was cloned as partial* (13.3 kDa) and full-length protein (20.3 kDa) with a 16.7 kDa thioredoxin fusion (His tag) resulting in 22.8 kDa protein for UH-CSFP1.7 and 30 kDa partial and 37 kDa full length band for UH-CSFP1.8 (SPAG16 protein) on SDS-PAGE after Coommassie staining.

Figure 3:
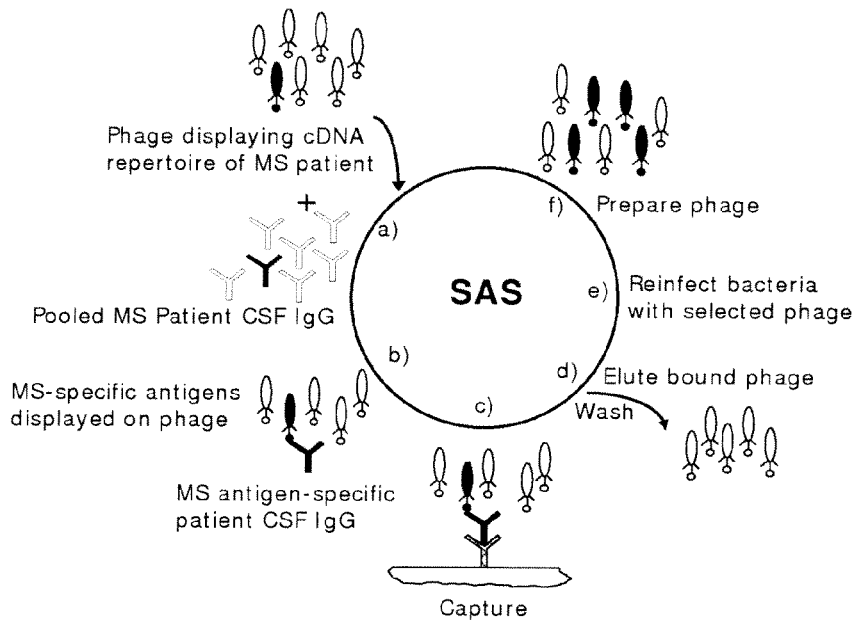

FIG. 3: SAS procedure. a. A phage-displayed MS cDNA repertoire is preincubated with MS patient CSF antibodies. b. MS-specific antigens displayed on phage (black) bind to MS-antigen specific patient IgG (black). c. Phage antigen-IgG complexes (black) are captured on a surface coated with polyclonal anti-human IgG (checked). d. Nonrelevant phages are washed away, and CSF-IgG specific phages are eluted. e. Selected phages are used for reinfection of bacteria. f. Selected phages are amplified and used for further rounds of selection.

Figure 4:
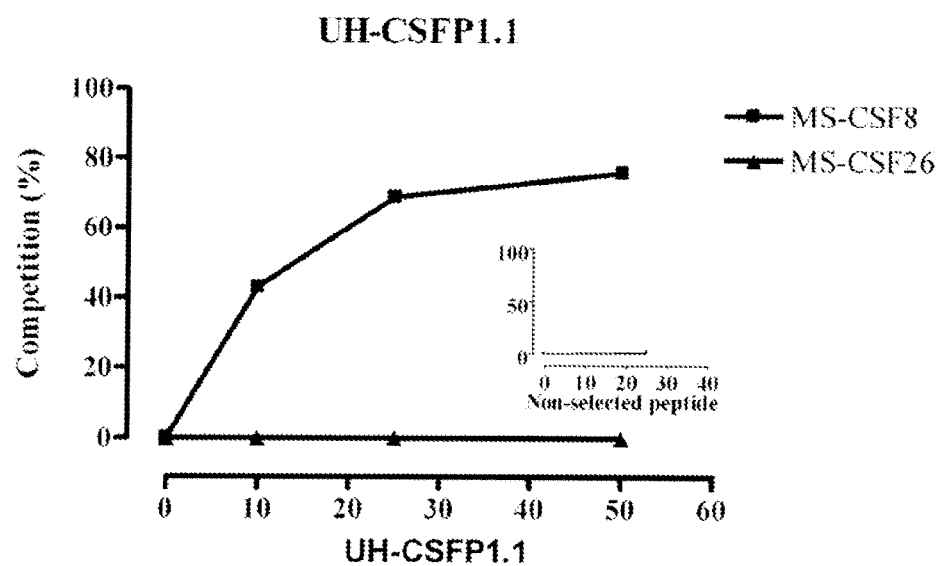

FIG. 4: Solution phase assays demonstrate high affinity and specificity of CSF antibodies to UH-CSFP1.1. The UH-CSFP1.1 peptide was pre-incubated at different dilutions with MS-CSF8 and MS-CSF26, respectively, and subsequently, the remaining immunoreactivity measured by ELISA. Competition by the UH-CSFP1.1 peptide is displayed. No competition was measured with the random peptide.

Figure 5:
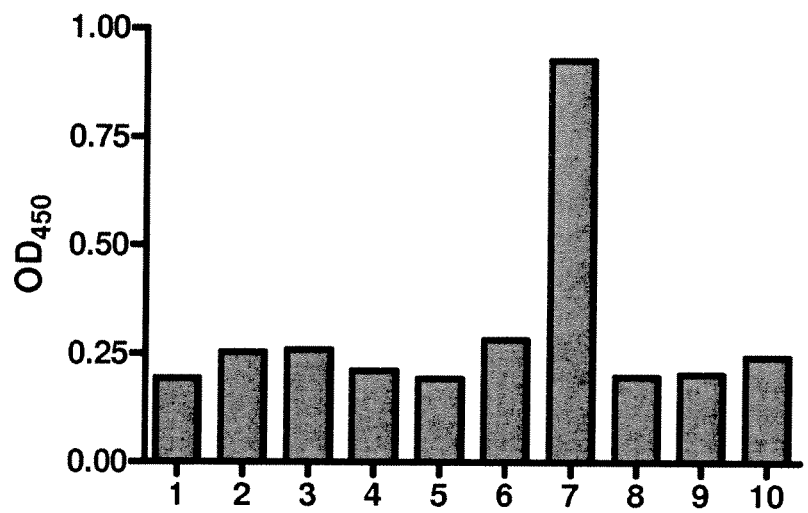

FIG. 5: Histogram showing reactivity against UH-CSFP1.1 peptide of 10 random clones tested by ELISA assay. A positive signal was obtained for clone 7.

Figure 6:
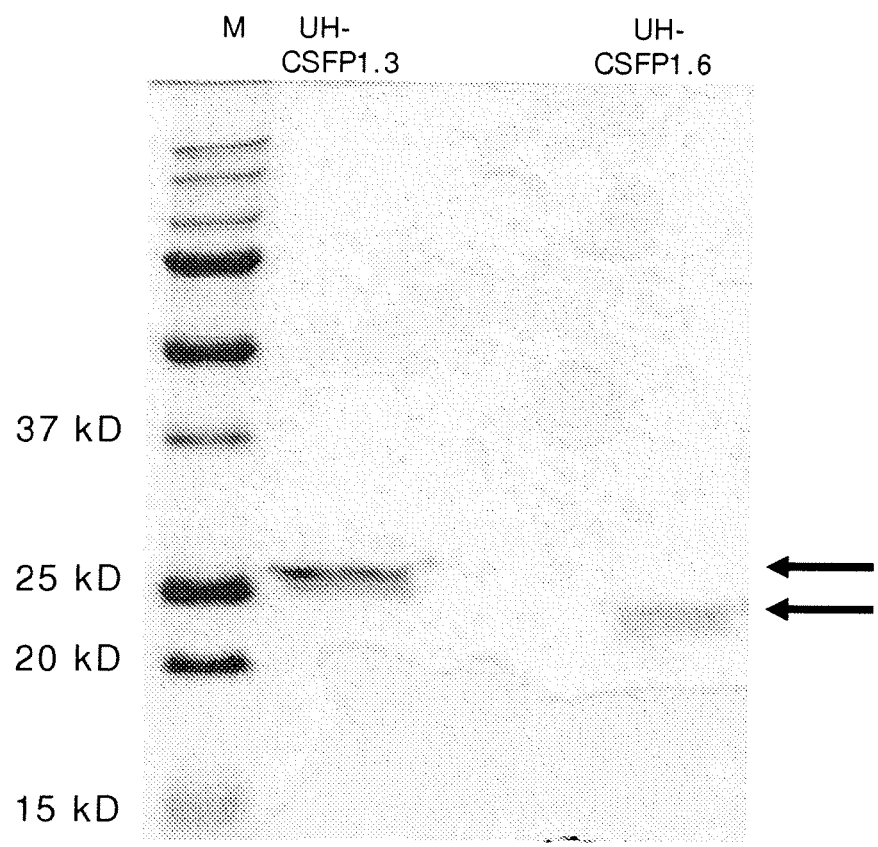

FIG. 6: Protein expression of UH-CSFP1.3 and UH-CSFP1.6 (partial).

Figure 7:
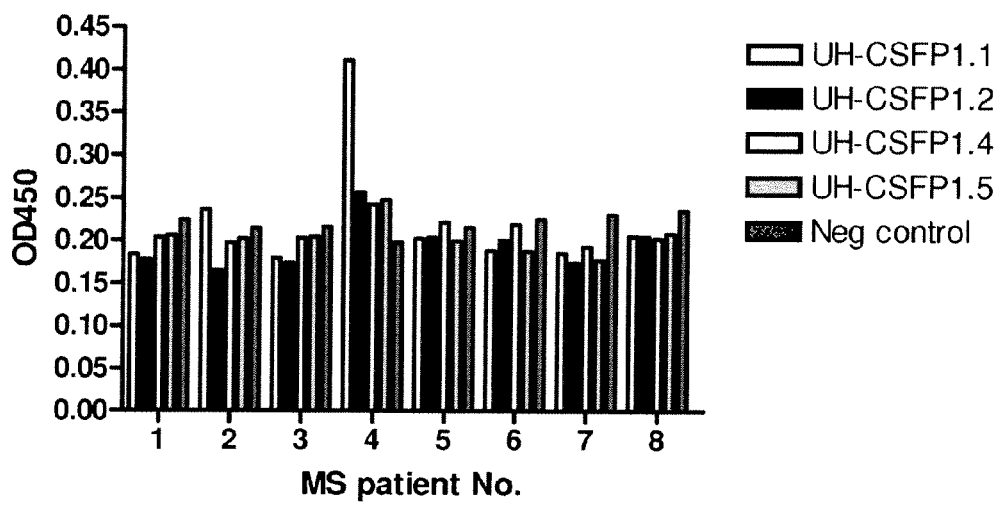

FIG. 7: Reactivity of 8 individual CSF samples against UH-CSFP1.1, UH-CSFP1.2, UH-CSFP1.4, UH-CSFP1.5 and negative control.

Figure 8:
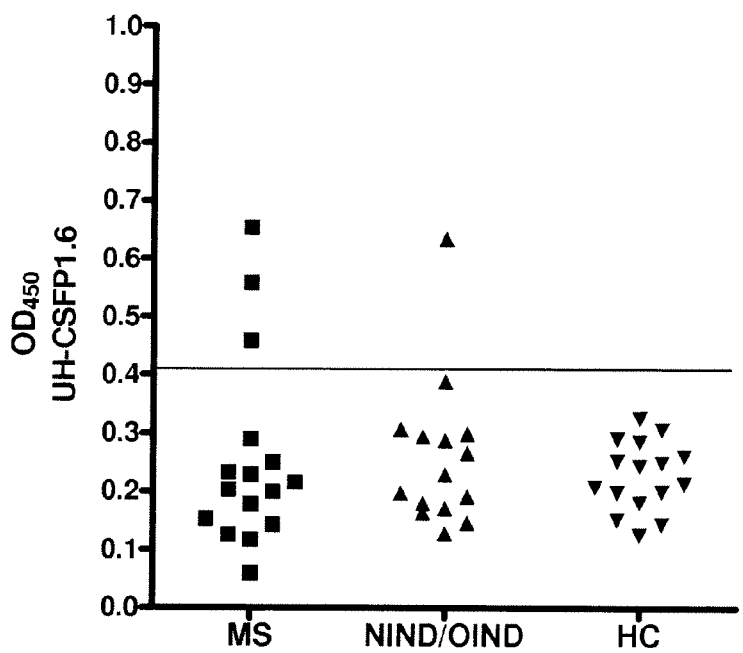

FIG. 8: Antibody reactivity towards UH-CSFP1.6 in serum from 16 randomly selected MS patients, 15 NIND/OIND patients and 16 healthy controls. The horizontal line represents the cut-off value.

AIMS AND DETAILED DESCRIPTION OF THE INVENTION

In the present invention we have identified a set of biomarkers which can be used for the detection of Multiple Sclerosis (MS) in patients. Biomarkers were isolated with the technology of Serological Antigen Selection (SAS) wherein antigens (i.e. biomarkers) were identified that bind to antibodies present in cerebrospinal fluid (CSF) in patients suffering from Multiple Sclerosis. More specifically, a cDNA phage display library comprising cDNA products derived from MS brain plaques—expressed as a fusion to minor coat protein pVI of filamentous phage M13—was panned to identify cDNA clones that bind auto-antibodies in CSF specimens from MS patients. A biomarker panel of 8 antigenic cDNA targets which showed 86% specificity and 45% sensitivity in discriminating MS patients and controls was retrieved. Besides a role in the immediate (early) diagnosis of patients suspected for MS, the biomarker panel (i.e. the antigenic cDNA targets) can be used to assist in sub-typing MS patients.

Thus in a first embodiment the invention provides a composition comprising at least two different polypeptides comprising a sequence represented by any of SEQ ID NO: 1-8 or a fragment comprising at least 5 consecutive amino acids derived from SEQ ID NO: 1-8. Such a composition is herein also designated as a biomarker or as a biomarker panel. The SEQ ID NO: 1-8 correspond with the translated amino acid sequences of the antigens retrieved by the selection of phage displayed MS cDNA expression library on MS patient cerebrospinal fluid (CSF). Thus the translation of the insert of UH-CSFP1.1 corresponds with SEQ ID NO: 1, . . . , and the translation of the insert of UH-CSFP1.8 corresponds with SEQ ID NO: 8 (see table 3). The nucleotide sequences which encode SEQ ID NO: 1-8 are depicted in SEQ ID NO: 9-16 (wherein SEQ ID NO: 9 encodes SEQ ID NO: 1, . . . , and SEQ ID NO: 16 encodes SEQ ID NO: 8). Thus a composition comprises at least two different polypeptides wherein such a polypeptide comprises a sequence as depicted by SEQ ID NO: 1, 2, 3, 4, 5, 6, 7 or 8. This means that a polypeptide present in the composition can also be a protein. As an example SEQ ID NO:8 was cloned as a partial 13.3 kDa protein (protein product as detected using SAS). Since SEQ ID NO: 8 (corresponding with UH-CSFP1.8) is a fragment of the SPAG16 protein (which full length is 37 kDa) the composition can also comprise the full length SPAG16 protein. The composition of the invention can also comprise at least two different polypeptides wherein said polypeptides are fragments comprising at least 5 consecutive amino acids derived from SEQ ID NO: 1, 2, 3, 4, 5, 6, 7 or 8. It is envisaged that 5 consecutive amino acids derived from SEQ ID NO: 1-8 are sufficient to be recognized as antigens by the auto-antibodies present in for example serum or CSF.

In a particular embodiment the composition comprises 8 different polypeptides comprising a sequence selected from SEQ ID NO: 1-8 or 8 different fragments comprising at least 5 consecutive amino acids derived from SEQ ID NO: 1-8.

In another particular embodiment the composition comprises 4 different polypeptides comprising a sequence represented by SEQ ID NO: 4, 5, 6 and 7 or 4 different fragments comprising at least 5 consecutive amino acids derived from SEQ ID NO: 4, 5, 6 and 7.

In another embodiment the invention provides the use of a composition of the invention for detecting the presence of specific antibodies to at least one polypeptide present in said composition wherein said antibodies are present in a body fluid of a mammal.

In another particular embodiment the invention provides the use of a composition of the invention for detecting the presence of specific auto-antibodies to at least one polypeptide present in said composition wherein said auto-antibodies are present in a body fluid of a mammal. In particular embodiments said use of a composition is an "in vitro" use of a composition. The latter implies a diagnostic method with no direct interaction with the patient. The term 'body fluid' includes blood, blood serum, blood plasma, saliva, urine, tears, bone marrow fluid, cerebrospinal fluid (CSF), synovial fluid, lymphatic fluid, amniotic fluid, nipple aspiration fluid and the like. Preferred body fluids for analysis are those that are conveniently obtained from patients, particularly preferred body fluids include blood serum, blood plasma and CSF.

In yet another embodiment the invention provides a method for detecting multiple sclerosis in a mammal comprising i) detecting the presence of at least one antibody in a body fluid derived from said mammal wherein said antibody has a specificity for a polypeptide comprising a sequence selected from the group consisting of SEQ ID NO: 1-8 or a fragment comprising at least 5 consecutive amino acids derived from SEQ ID NO: 1-8 and wherein ii) the presence or quantity of said antibody indicates that said mammal suffers from multiple sclerosis.

In yet another embodiment the method for detecting multiple sclerosis in a mammal of the present invention is combined with the detection of the MS markers described in US20040043431 and more specifically to the markers described in the claims 5, 6, 7, 8, 9 and 10 of said application.

In yet another embodiment the invention provides a method for evaluating the prognosis/disease severity of multiple sclerosis in a mammal comprising i) detecting the presence or quantity of at least one antibody in a body fluid derived from said mammal wherein said antibody has a specificity for a polypeptide comprising a sequence selected from the group consisting of SEQ ID NO: 1-8 or a fragment comprising at least 5 consecutive amino acids derived from SEQ ID NO: 1-8 and wherein ii) the increased or decreased concentration of said antibody indicates the prognosis of multiple sclerosis in said mammal.

In yet another embodiment the invention provides a method for selecting mammals for a specific therapeutic treatment of multiple sclerosis or evaluating the therapeutic treatment of multiple sclerosis in a mammal comprising i) detecting the presence or quantity of at least one antibody in a body fluid derived from said mammal wherein said antibody has a specificity for a polypeptide comprising a sequence selected from the group consisting of SEQ ID NO: 1-8 or a fragment comprising at least 5 consecutive amino acids derived from SEQ ID NO: 1-8 and wherein ii) the increased or decreased concentration of said antibody leads to an election of a specific therapeutic treatment of multiple sclerosis in said mammal.

In a preferred embodiment said body fluid is CSF.

In yet another preferred embodiment said body fluid is serum.

In another preferred embodiment said mammal is a human.

In yet another embodiment the invention provides an antibody that specifically binds to a polypeptide selected from the group comprising of polypeptides selected from the group consisting of SEQ ID NO: 1-8 or a fragment comprising at least 5 consecutive amino acids derived from SEQ ID NO: 1-8. Methods for generating antibodies are well known in the art. In a preferred embodiment the antibodies are monoclonal antibodies. For the purpose of generation of antibodies the polypeptides forming part of the compositions of the invention may be synthesized chemically or may be made in a recombinant way. They may also be coupled to a soluble carrier after synthesis or after recombinant production. If a carrier is used the nature of such a carrier should be such that it has a molecular weight greater than 5000 and should not be recognized by antibodies. Such a carrier can be a protein. Proteins which are frequently used as carriers are keyhole limpet hemocyanin, bovine gamma globulin, bovine serum albumin, and poly-L-lysine. There are many well described techniques for coupling peptides to carriers. The linkage may occur at the N-terminus, C-terminus or at an internal site in the peptide. The polypeptide may also be derivatized for coupling. The polypeptides may also be synthesized directly on an oligo-lysine core in which both the alpha as well as the epsilon-amino groups of lysines are used as growth points for the polypeptides. The number of lysines comprising the core is preferably 3 or 7. Additionally, a cysteine may be included near or at the C-terminus of the complex to facilitate the formation of homo- or heterodimers.

In general terms the invention relates to a process for detecting antibodies related to MS in a biological sample of a mammal liable to contain them, this process comprising contacting the biological sample with a composition according to the invention under conditions enabling an immunological reaction between said composition and the antibodies which are possibly present in the biological sample and the detection of the antigen/antibody complex which may be formed. The detection can be carried out according to any classical process. By way of examples immunoenzymatic processes according to the ELISA technique or immunofluorescent or radioimmunological (RIA) or the equivalent ones (e.g. LINE blot or LINE assay) can be used. Thus the invention also relates to polypeptides according to the invention labeled by an appropriate label of the enzymatic, fluorescent, biotin, radioactive type. Such a method for detecting antibodies related to MS comprises for instance the following steps: deposit of determined amounts of a polypeptidic composition according to the invention on a support (e.g. into wells of a titration microplate), introduction on said support (e.g. into wells) of increasing dilutions of the body fluid (e.g. CSF) to be diagnosed, incubation of the support (e.g. microplate), repeated rinsing of the support (e.g. microplate), introduction on the support labeled antibodies which are specific for immunoglobulins present in the body fluid, the labeling of these antibodies being based on the activity of an enzyme which is selected from among the ones which are able to hydrolyze a substrate by modifying the absorption of the radiation of this latter at least at a given wave length, detection by comparing with a control standard of the amount of hydrolyzed substrate.

In yet another embodiment the invention also relates to a process for detecting and identifying antigens of MS in a body fluid liable to contain them, this process comprising: contacting the biological sample with an appropriate antibody of the invention (i.e. antibodies with a specificity for a polypeptide of the composition) under conditions enabling an immunological reaction between said antibody and the antigens of MS which are possibly present in the biological sample and the detection of the antigen/antibody complex which may be formed.

Thus antibodies, in particular auto-antibodies, which recognize the polypeptides of the invention, can be detected in a variety of ways. One method of detection is further described in the examples and uses enzyme-linked immunosorbant assay (ELISA) of the polypeptides of the invention displayed by phages (i.e. phage-ELISA technology). The latter technology is fully described in Somers V. et al (2005) *J. of Autoimmunity* 25: 223-228, wherein paragraph 2.6 on page 225 is herein specifically incorporated). In other ways in the detection in ELISA a polypeptide or a mixture of polypeptides is bound to a solid support. In some cases, this will be a microtiter plate but may in principle be any sort of insoluble solid phase (e.g. glass, nitrocellulose). In one embodiment a suitable dilution or dilutions of for example CSF or serum to be tested is brought into contact with the solid phase to which the polypeptide is bound. In another embodiment "a solution hybridization" is carried out in which high affinity interactions occur (e.g. biotinylated polypeptides of the composition are pre-incubated with CSF). The incubation is carried out for a time necessary to allow the binding reaction to occur. Subsequently, unbound components are removed by washing the solid phase. The detection of immune complexes (i.e. auto-antibodies present in for example human CSF binding to at least one polypeptide of the invention) is achieved using antibodies which specifically bind to human immunoglobulins, and which have been labeled with an enzyme, preferably but not limited to either horseradish peroxidase, alkaline phosphatase, or beta-galactosidase, which is capable of converting a colorless or nearly colorless substrate or co-substrate into a highly colored product or a product capable of forming a colored complex with a chromogen. Alternatively, the detection system may employ an enzyme which, in the presence of the proper substrate(s), emits light. The amount of product formed is detected either visually, spectrophotometrically, electrochemically, fluorescently or luminometrically, and is compared to a similarly treated control. The detection system may also employ radioactively labeled antibodies, in which case the amount of immune complex is quantified by scintillation counting or gamma counting. Other detection systems which may be used include those based on the use of protein A derived from *Staphylococcus aureus* Cowan strain I, protein G from group C *Staphylococcus* sp. (strain 26RP66), or systems which make use of the high affinity biotin-avidin or streptavidin binding reaction.

The polypeptides of the invention may be either labeled or unlabeled. Labels which may be employed may be of any type, such as enzymatic, chemical, fluorescent, luminescent, or radioactive. In addition, the polypeptides may be modified for binding to surfaces or solid phases, such as, for example, microtiter plates, nylon membranes, glass or plastic beads, and chromatographic supports such as cellulose, silica, or agarose. The methods by which polypeptides can be attached or bound to solid support or surface are well known to those skilled in the art.

The polypeptides of the invention can be prepared according to the classical techniques in the field of peptide synthesis. The synthesis can be carried out in homogeneous solution or in solid phase. For instance, the synthesis technique in homogeneous solution which can be used is the one described by Houbenweyl in the book titled "Methode der organischen chemie" (Method of organic chemistry) edited by E. Wunsh, vol. 15-I et II. THIEME, Stuttgart 1974. The polypeptides of the invention can also be prepared in solid phase according to the method described by Atherton & Shepard in their book titled "Solid phase peptide synthesis" (Ed. IRL Press, Oxford, N.Y., Tokyo, 1989). Synthesis protocols in the art generally employ the use of t-butyloxycarbonyl- or 9-fluorenyl-methoxy-carbonyl-protected activated amino acids. The procedures for carrying out the syntheses, the types of side-chain protection, and the cleavage methods are amply described in, for example, Stewart and Young, Solid Phase Peptide Synthesis, 2nd Edition, Pierce Chemical Company, 1984; and Atherton and Sheppard, Solid Phase Peptide Synthesis, IRL Press, 1989.

In yet another embodiment antibodies raised to polypeptides of the invention (or carrier-bound polypeptides) can also be used in conjunction with labeled polypeptides of the invention for the detection of (auto)-antibodies present in serum or CSF by competition assay. In this case, antibodies raised to polypeptides are attached to a solid support which may be, for example, a plastic bead or a plastic tube. Labeled polypeptide is then mixed with suitable dilutions of the fluid (e.g. CSF) to be tested and this mixture is subsequently brought into contact with the antibody bound to the solid support. After a suitable incubation period, the solid support is washed and the amount of labeled polypeptide is quantified. A reduction in the amount of label bound to the solid support is indicative of the presence of (auto)-antibodies in the original sample. By the same token, the polypeptide may also be bound to the solid support. Labeled antibody may then be allowed to compete with (auto)-antibody present in the sample (e.g. CSF) under conditions in which the amount of polypeptide is limiting. As in the previous example, a reduction in the measured signal is indicative of the presence of (auto)-antibodies in the sample tested.

In a particular embodiment a test for giving evidence of the fact that one or more polypeptides present in a composition of the invention are recognized by antibodies present in for example CSF of serum (for example auto-antibodies present in CSF of multiple sclerosis patients) is an immunoblotting (or Western blotting) analysis. In the latter case polypeptides can be chemically synthesized or polypeptides (or the protein) can be produced via recombinant techniques. In short, after sodium dodecyl sulfate-polyacrylamide gel electrophoresis, polypeptides of the invention are blotted onto nitrocellulose membranes (e.g. Hybond C. (Amersham)) as described by Towbin H. et al., 1979, "Electrophoretic transfer of proteins from polyacrylamide gels to nitrocellulose sheets: procedure and some applications", Proc. Natl. Acad. Sci. USA 76:4350-4354. In order to identify selective recognition of polypeptides (or proteins) of the invention by CSF, nitrocellulose sheets are incubated overnight with each of these samples (e.g. diluted 1:50) (after blocking a-specific protein-binding sites). Reactive areas on the nitrocellulose sheets are revealed by incubation with e.g. peroxidase conjugated goat anti-human immunoglobulin G antibody (e.g. diluted 1:200) for 4 h, and after repeated washings, color reaction is developed by adding for example alpha-chloronaphtol (Bio-Rad Laboratories, Richmond, Calif.) in the presence of hydrogen peroxide.

It goes without saying that the free reactive functions which are present in some of the amino acids, which are part of the constitution of the polypeptides of the invention, particularly the free carboxyl groups which are carried by the groups Glu and Asp or by the C-terminal amino acid on the one hand and/or the free NH2 groups carried by the N-terminal amino acid or by amino acids inside the peptidic chain, for instance Lys, on the other hand, can be modified in so far as this modification does not alter the above mentioned properties of the polypeptide. The polypeptides which are thus modified are naturally part of the invention. The above mentioned carboxyl groups can be acylated or esterified. Other modifications are also part of the invention. Particularly, the amine or carboxyl functions or both of terminal amino acids can be themselves involved in the bond with other amino acids. For instance, the N-terminal amino acid can be linked to the C-terminal amino acid of another peptide comprising from 1 to several amino acids.

Furthermore, any peptidic sequences resulting from the modification by substitution and/or by addition and/or by deletion of one or several amino acids of the polypeptides according to the invention are part of the invention in so far as this modification does not alter the above mentioned properties of said polypeptides. The polypeptides according to the invention can be glycosylated or not, particularly in some of their glycosylation sites of the type Asn-X-Ser or Asn-X-Thr, X representing any amino acid.

An advantageous recombinant polypeptide included in the composition of the invention is SEQ ID NO: 6 since this polypeptide shows the highest frequency of antibody responses in CSF of MS patients with no reactivity in the control patients.

Variations of these polypeptides are also possible depending on its intended use. For example, if the polypeptide is to be used to raise antisera, the polypeptide may be synthesized with an extra cysteine residue added. This extra cysteine residue is preferably added to the amino terminus and facilitates the coupling of the polypeptide to a carrier protein which is necessary to render the small polypeptide immunogenic. If the polypeptide is to be labeled for use in radioimmune assays, it may be advantageous to synthesize the protein with a tyrosine attached to either the amino or carboxyl terminus to facilitate iodination. This polypeptide possesses therefore the primary sequence of the polypeptide above-mentioned but with additional amino acids which do not appear in the primary sequence of the protein and whose sole function is to confer the desired chemical properties to the polypeptide.

In yet another embodiment the invention provides for a kit to diagnose MS. To carry out the diagnostic method for MS, the following necessary or kit can be used, said necessary or kit comprising: a composition (comprising at least one polypeptide selected from SEQ ID NO: 1-8) according to the invention, or at least one fragment comprising at least 5 consecutive amino acids derived from SEQ ID NO: 1-8, reagents for making a medium appropriate for the immunological reaction to occur, reagents enabling to detect the antigen/antibody complex which has been produced by the immunological reaction, said reagents possibly having a label, or being liable to be recognized by a labeled reagent, more particularly in the case where the above mentioned polypeptide is not labeled.

Other characteristics and advantages of the invention will appear in the following examples and the figures illustrating the invention.

EXAMPLES

1. Enrichment of a Phage Displayed MS cDNA Library with MS CSF

To create an MS cDNA display library, a normalized cDNA library derived from active, chronic MS plaques, with varying degrees of demyelination and inflammatory activity, which was originally cloned into the pT7T3-Pac vector, was cloned into the M13 filamentous phage display vectors pSPA, B and C. These vectors allow expression of cDNA products (peptides) derived from MS brain plaques as a fusion to minor coat protein pVI of filamentous phage M13 in 3 reading frames for correct expression of the protein products. A total library size of $1.1 \times 10^7$ colony forming units (cfu) was obtained.

To enrich the MS cDNA display library for cDNA products (displayed peptides) that are specifically bound by autoantibodies present in cerebrospinal fluid of MS patients, we performed successive rounds of selection (see FIG. 3, and Table 7) on pooled CSF of 10 randomly selected RR MS patients. Following rescue of the phage clones after each of 4 rounds of selection, enriched phage clones, each bearing a single fusion peptide derived from the MS cDNA display library, were randomly selected for further study.

2. Characterization of the Enriched Phage Clones

Among the enriched clones, a total of 52 clones were selected. cDNA inserts were sequenced and the translated protein sequences were determined. Sequence analysis revealed 8 antigenic targets, which we annotated with the name UH-CSFP-number, which is short for University Hasselt-cerebrospinal fluid pool-number of the clone. These sequences corresponded to known proteins expressed in the correct reading frame, but also homology to untranslated regions of expressed genes, such as 3' UTR sequence of proteolipid protein, or homology to out of frame sequences were obtained (see table 3).

In initial experiments, we assessed the reactivity of the individual MS CSF specimens used for the selection procedure against 8 enriched antigenic cDNAs. As shown in Table 4, of the 10 CSF samples from RR-MS patients, 8 contained antibodies that reacted with at least 2 phage-peptide clones. These clones were used for subsequent screening on a large panel of CSF from other MS patients as well as CSF from patients with other inflammatory (OIND) and non-inflammatory neurological disorders (NIND).

Of the 10 RR-MS patients used for the selection procedure, paired serum samples were also collected and used for screening for antibody reactivity towards the 8 enriched antigenic cDNAs. In 3 out of 8 patients with antigen specific antibodies present in CSF, reactivity towards 1 of the 8 antigenic cDNAs was also found in paired serum. There was a good association between the positive signal observed in the CSF, and the reactivity demonstrated in serum. The signal on individual CSF tested was higher than that on individual serum tested, which is consistent with the dilution of the antigen specific antibodies present in the serum, when antibodies are intrathecally produced. When low reactivity in the CSF was observed, no positive signal was found in the serum of the same patient. In addition, no reactivity in paired serum samples was demonstrated in patients with antibody negative CSF (data not shown).

3. Detailed Serological Analysis of the MS Panel

Next, clones were tested on a large panel of individual CSF specimens not used for the selection procedure (n=63 for MS patients (54 RR-MS, 3 SP-MS patients and 6 PP-MS), n=30 for OIND patients and n=64 for NIND patients). The results of the phage ELISA screening of the individual phage-cDNA clones on 167 different CSF are presented in Table 5. All antigens tested showed exclusive or preferential reactivity in the MS group as compared to the control group. Clones UH-CSFP1.4-UH-CSFP1.7 showed reactivity in 17 of 73 (23%) MS CSF whereas no reactivity towards the OIND and NIND CSF specimens was observed. The remaining clones (UH-CSFP1.1-UH-CSFP1.3 and UH-CSFP1.8) showed higher reactivity in the MS group 25/73 (34%) as compared to the control group 13/94 (14%), and therefore, these clones were also defined as clones with an MS-related serological profile.

In total, 33 of 73 (45%) MS patients showed CSF IgG antibodies reactive with at least one of the panel of 8 antigenic targets. The highest frequency of antibody responses in MS CSF with no reactivity in the control group was found to UH-CSFP1.6. All CSF samples tested showed equivalent total CSF IgG levels. CSF samples with high IgG concentration were normalized to the normal CSF concentration range.

4. Expression Pattern of Novel MS Markers

Northern blot analysis of the antigenic targets with no reactivity in the control group was performed on a variety of normal human tissues. UH-CSFP1.4 gave a transcript of 1.9 kb and was highly expressed brain, heart and placenta, and to a lower extent in skeletal muscle, kidney and liver. UH-CSFP1.7 gave a transcript size of 5.1 kb and showed a high expression in brain, heart and skeletal muscle. No transcript could be detected for UH-CSFP1.5 and UH-CSFP1.6.

We further selected 4 of the antigenic targets (UH-CSFP1.3, UH-CSFP1.6, UH-CSFP1.7 and UH-CSFP1.8), for protein expression in *E. coli*. UH-CSFP1.7 was cloned as antigen (6.1 kDa) and the UH-CSFP1.8 (SPAG16) protein was cloned as partial (13.3 kDa, protein product as detected using SAS) and full-length protein (20.3 kDa) with a 16.7 kDa thioredoxin fusion (His tag) resulting in 22.8 kDa protein for UH-CSFP1.7 and 30 kDa partial and 37 kDa full length band for SPAG16 protein on SDS-PAGE after Coommassie staining (see FIG. 2).

Due to the presence of amber stop codons in the sequences of clones UH-CSFP1.3 and UH-CSFP1.6, site-directed mutagenesis was performed to create glutamine codon(s) for use in bacterial protein expression in the non-suppressing LMG194 strain. Following site-directed mutagenesis, UH-CSFP1.3 was cloned as antigen (6.11 kDa) resulting in a 22.8 kDa protein including thioredoxin (see FIG. 6). Due to toxicity, the entire UH-CSFP1.6 could not be expressed. Therefore, the first part of the protein encoded by amino acids 1-52 of the antigen (as detected using SAS) was produced, resulting in a 22.5 kDa protein product including thioredoxin (see FIG. 6).

5. Autoantibody Reactivity and Clinical Data

We next determined whether reactivity to our antigenic panel was associated with a particular disease phenotype. Autoantibody reactivity to at least 1 of the 8 antigenic targets was demonstrated in 30/64 (47%) RR-MS patients, 3/6 (50%) PP-MS patients and 0/3 SP-MS patients. Demographic variables and EDSS score in antibody-positive and antibody-negative MS patients are shown in Table 6. No differences were observed in age between antibody-positive and antibody-negative patients. Antibody reactivity could be observed in some patients at time of diagnosis and was present in patients with short disease duration (<1 year), but also in patients with a disease duration greater than 10 years. However, no correlation was found between antibody reactivity and disease duration.

In order to assess the influence of antibody reactivity on disease severity, we examined the relationship between antibody reactivity and EDSS score. Antibody reactivity was found in 21/50 (42%) of patients with EDSS<3, 6/11 (54%) of patients with EDSS=3 or 3,5, and 3/5 (60%) of MS patients with EDSS=4. Although a higher percentage of patients showed reactivity to the panel of 8 antigenic cDNAs with increasing EDSS score, this difference was not significant.

6. Solution Phase Assay/Competition ELISA

To determine whether the observed autoantibody signature of MS CSF is due to the MS brain plaque derived peptides, 2 MS CSF specimens (one positive (MS-CSF8) and one negative (MS-CSF26) for UH-CSFP1.1 were pre-incubated with the synthetic peptide UH-CSFP1.1 (NH2-ASSRGYEDL-RTF-COOH) representing the cDNA insert of clone UH-CSFP1.1 and with a non-specific (random) peptide. As shown in FIG. 4, preincubation with UH-CSFP1.1 peptide clearly inhibited the formation of specific IgG antibody/phage UH-CSFP1.1 complexes for MS-CSF8 while no inhibition was found for MS-CSF26. In contrast, CSF reactivity against clone UH-CSFP1.1 was not inhibited by addition of the random peptide.

7. Monoclonal Antibody Production

A murine monoclonal antibody for UH-CSFP1.1 was produced based on the hybridoma technology developed by Kohler and Milstein (Kohler, G and Milstein, C, 1973, Nature 256, 495-497). FIG. 5 represents antibody reactivity against UH-CSFP1.1 peptide following hybridoma selection. The ODs of supernatants from 10 random tested clones of hybridomas are indicated at first screening for antibody production. A positive ELISA signal was obtained for clone 7. Further subcloning of this clone resulted in a monoclonal hybridoma cell line producing antibodies directed against UH-CSFP1.1 peptide. The produced monoclonal antibody showed the same epitope specificity as previously identified for MS serum or CSF samples. This allows further analysis of the UH-CSFP1.1 antigen. In an alternative approach, we are using phage particles expressing the UH-CSFP antigenic targets for immunization of Balb/c female mice. Advantages of using phage-displayed peptides is that they are cheap, easy to obtain and that the antigen is displayed to the murine immune system as it is recognized in serum or CSF from MS patients.

8. ELISA on Peptides

To address whether antibody reactivity was also observed against linear peptides, we used ELISA on synthetic peptides (UH-CSFP1.1, UH-CSFP1.2, UH-CSFP1.4 and UH-CSFP1.5). As shown in FIG. 7, MS patient No. 4 showed CSF reactivity against clone UH-CSFP1.1, while for the other peptides, no reactivity was found. For the other MS patients, no reactivity was seen against any of the tested peptides. These results were consistent with the phage ELISA results for UH-CSFP1.1, UH-CSFP1.2, UH-CSFP1.4 and UH-CSFP1.5.

9. ELISA on Purified Recombinant Proteins

After protein expression of UH-CSFP1.3, UH-CSFP1.6, UH-CSFP1.7 and UH-CSFP1.8 (as described in example 4, second paragraph), immunoreactivity for each purified recombinant protein was measured in serum. FIG. 8 represents antibody reactivity towards UH-CSFP1.6 in serum from 16 randomly selected MS patients, 15 NIND/OIND patients and 16 healthy controls. Reactivity was demonstrated in 3/16 MS patients and 1/15 NIND/OIND patients, while no reactivity was found in healthy controls.

10. Immunohistochemical Staining

After monoclonal antibody production (example 7), the murine monoclonal antibody against UH-CSFP1.1 was used for immunohistochemical staining of experimental autoimmune encephalomyelitis (EAE) rat brain tissue. It was observed that the murine monoclonal antibody against UH-CSFP1.1 stained the endothelial lining of blood vessels and showed cytoplasmic staining of large neurons.

Materials and Methods
1. Patients and Controls

Cerebrospinal fluid samples were obtained from 73 MS patients, 30 patients with other inflammatory (meningitis, polyneuropathy) and 64 patients with non-inflammatory neurological disorders (hernia, epilepsy, dementia, headache, Alzheimer patients, . . . ) undergoing lumbar puncture for diagnostic purposes. MS patients were diagnosed according to the McDonald and Poser criteria[14]. Characteristics of the study population are shown in table 1. From 28 out of 73 MS patients, paired serum samples were collected. CSF and serum samples were stored at −80° C. after collection. The study was approved by the institutional ethics committee.

2. Cloning of an MS cDNA Library for pVI Display and Serological Antigen Selection (SAS) of Phage pVI Displayed cDNA Repertoires A normalized cDNA library ($1.0 \times 10^6$ primary recombinants) derived from 3 active chronic MS plaques, with varying degrees of demyelination and inflammatory activity (gift from Dr. Soares) was used to construct an MS cDNA display library by cloning it as a fusion protein with filamentous phage minor protein pVI. Therefore, the library was transferred to our phage display vectors, named pSPVIA, pSPVIB and pSPVIC, each encoding one of three reading frames. Details of the cloning procedure are described in[15].

The SAS procedure was performed as described previously (Somers, J I)[15]. In brief, CSF samples of 10 randomly selected untreated relapsing remitting (RR)-MS patients were pooled and used for affinity selections. Characteristics of the patients used for affinity selections are shown in table 2. Before the start of the selection procedure, CSF samples were absorbed against *Escherichia coli* (*E. coli*) and phage antibodies as described in[15]. Following adsorption, pooled CSF was stored at −20° C. Subsequently, pooled preabsorbed CSF was used for the selection procedure. Affinity selections were performed as described before[15]. In brief, an immunotube (Nunc, Roskilde, Denmark) was coated with rabbit anti-human IgG (Dako, Glostrup, Denmark) in coating buffer (0.1M sodium hydrogen carbonate pH 9.6) for 2 hours at 37° C. After washing the immunotube twice with phosphate-buffered saline containing 0.1% Tween 20 and twice with PBS, the tubes were blocked for 2 hours with 2% MPBS (2% milk powder in PBS). For the first round of the selection procedure, phage were prepared from the MS cDNA library cloned in the 3 phage display vectors pSP6A, B and C. Phage were prepared as described previously[16]. Approximately $10^{13}$ phage were added to pooled preadsorbed CSF (1:5 diluted in 4% MPBS) and incubated for 1.5 hour at RT on a rotating platform. After washing the coated immunotube twice with PBST and twice with PBS, the preincubated CSF and phage mix was transferred to the coated immunotube and incubated for 30 minutes on a rotating platform and 120 minutes standing at RT. Tubes were then washed extensively with PBST and PBS to remove non-binding phage. Binding phage were eluted with 100 mM triethylamine and neutralized with 1M Tris HCl as described before[17]. *E. coli* TG1 cells were infected with input and output phage and plated on 2×TY agar plates containing ampicillin and glucose (16 g/l bacto-tryptone, 10 g/l yeast extract, 5 g/l NaCl, 15 g bacto-agar/l, ampicillin at 100 µg/ml and glucose at 2%) at each round of selection. Resultant colonies were scraped and phages were rescued for further rounds of affinity selections. To monitor enrichment of specific clones, input and output phage from each round of selection were titrated and the ratio of output/input phage was determined. After several rounds of selection, individual colonies were selected and the insert size and sequence was determined as described in[15]. Sequences were submitted to GenBank for BLAST homology search.

3. Phage ELISA

ELISA of ligand displaying phage was performed as described in[15]. Immunoreactivity for each phage peptide was measured in relation to an internal control signal detected by antibody reactivity against the empty phage. For competition ELISA, CSF was pre-incubated in the presence of 0-50 pmol/50 µl synthetic peptide UH-CSFP1.1 (NH2-ASSRGYEDL-RTF-COOH) or random peptide. Subsequently, the immunoreactivity to phage UH-CSFP1.1 was determined according to the standard phage ELISA procedure.

4. Northern Blot Analysis

Plasmid was isolated using the Qiagen Plasmid Midi Kit according to the manufacturer's instructions. The isolated plasmid was EcoRI/NotI digested and the excised DNA was gel-purified (GFX™ PCR DNA and Gel Band Purification Kit, GE Healthcare, Brussel, Belgium). The excised DNA fragment was used as probe in Northern blot. Probes were labelled with [$\alpha^{32}$P] using the High Prime DNA Labeling Kit (Roche, Vilvoorde, Belgium). Briefly, 50 ng excised DNA was first denatured during 10 min in boiling water and immediately chilled on ice. The labelling mix was added to the DNA and after 45 min incubation at 37° C., the reaction was stopped by addition of 0.2 M EDTA. Labelled DNA was purified with Sephadex G75 columns and radioactivity measured with a scintillation counter.

Northern blotting was performed using the Multiple Tissue Northern (MTN™) Blot (BD Biosciences, Erembodegem, Belgium). Briefly, labelled DNA or human β-actin cDNA control probe was denatured at 97° C. during 5 min and immediately chilled on ice for a few minutes. After prehybridisation of the blotting membrane with ExpressHyb solution, the radioactively labelled probe was added (2-10 ng/ml or 1-2×$10^6$ cpm/ml) and hybridization occurred overnight at 68° C. After washing 3 times, the blotting membrane was exposed to X-ray film at −70° C. and developed using the Gevamatic 60 (Agfa Gevaert, Mortsel, Belgium).

5. Cloning of Antigenic cDNAs in pBAD/Thio-TOPO Vector and Expression of Recombinant Proteins Several of the antigenic cDNAs were cloned into the pBAD/Thio-TOPO vector (Invitrogen Life Technologies, Merelbeke, Belgium) and transformed into LMG194 cells according to the manuacturer's directions. Clones were cultured in LB Broth Base medium (Invitrogen Life Technologies, Merelbeke, Belgium) supplemented with ampicillin. Expression in *E. coli*, driven by the araBAD promoter ($p_{BAD}$), was induced by addition of 0.2% arabinose. Recombinant proteins were expressed as fusions to His-Patch thioredoxin and were purified by Ni-NTA beads (Qiagen, Venlo, the Netherlands) according to the manufacturer's instructions. Expression of the proteins of the correct size was confirmed by SDS-PAGE. Protein identity was confirmed by mass spectrometry.

Due to the presence of amber stop codons in the nucleotide sequences of clones UH-CSFP1.3 and UH-CSFP1.6, site-directed mutagenesis (Quikchange Site-Directed Mutagenesis Kit, Stratagene) was performed according to the manufacturer's directions in order to create glutamine codon(s) for use in bacterial protein expression in the non-suppressing LMG194 strain. For UH-CSFP1.6 the first part of the protein encoded by amino acids 1-52 of the antigen (as detected using SAS) was produced.

6. Statistical Analysis

Statistical analysis was performed using GraphPad Prism version 4.0. Quantitative demographic variables for antibody-positive and antibody-negative individuals were compared using t-tests, and categorical variables were compared using chi-square tests. A p value <0.05 was considered statistically significant. Correlations between various markers were determined by linear regression analysis.

7. Monoclonal Antibody Production

A murine monoclonal antibody for UH-CSFP1.1 was produced according to the hybridoma technology developed by Kohler and Milstein (Kohler, G and Milstein, C, 1973, Nature 256, 495-497). Due to its small size, UH-CSFP1.1 peptide was coupled to keyhole limpit hemocyanin (KLH) as carrier (UH-CSFP1.1) (Eurogentec) for immunization of Balb/c female mice. After three intraperitoneal immunizations with 150 μg UH-CSFP1.1-KLH, spleen cells were isolated and fused with a mouse myeloma cell line (Sp2/0). After selection of fused hybridomas by culturing in HAT medium, screening of the resulting hybridoma cell lines was performed by peptide ELISA using coated UH-CSFP1.1 peptide (Eurogentec) and cell line supernatant. After subcloning, a monoclonal hybridoma cell line was obtained, which produced antibodies directed against UH-CSFP1.1 peptide.

8. ELISA on Peptides

For ELISA experiments, 96-well ELISA plates (Greiner) are coated with 100 μl of 1 μg/ml peptide (UH-CSFP1.1, UH-CSFP1.2, UH-CSFP1.4 and UH-CSFP1.5) in PBS and kept overnight at RT. Wells are then washed with 3 times with PBS 0.05% Tween 20 and blocked at RT with blocking buffer (2% nonfat milk in PBS). After washing 3 times with PBS 0.05% Tween20, the plates are incubated with 100 μl diluted samples (CSF 1:5 diluted and serum, 1:100 diluted in blocking buffer) for 2 hours at RT. After several washings with PBS-T, wells are incubated with 100 μl of 1:2000 dilution of HRP-conjugated anti-human IgG in blocking buffer for 1 hour. After washing, 100 μl TMB-developing solution is added to each well, which is then incubated at RT. The reaction is stopped by the addition of 1M $H_2SO_4$ and read at 450 nm. For negative controls, wells are not incubated with sample, and other wells are not coated with antigen but are incubated with sample. For negative control values, the mean of both negative control values are presented.

9. ELISA on Purified Recombinant Proteins

ELISA experiments were performed as described for peptides, except that 96-well ELISA plates (Greiner) were coated with 100 μl of 1 μg/ml purified proteins (UH-CSFP1.3, UH-CSFP1.6, UH-CSFP1.7 and UH-CSFP1.8) in coating buffer and kept overnight at 4° C. Serum samples were considered positive for antibodies against the purified proteins when the $OD_{450}$ was higher than the mean+3 times the standard deviation of the healthy controls. The horizontal line in FIG. 8 represents the cut-off value.

TABLE 1

Characteristics of the study population

| Diagnosis | No. | Female/Male | Mean age (SD) (range) in years |
|---|---|---|---|
| MS | 73 | 51/22 | 38.6 (9.5) (16-57) |
| RR-MS | 64 | | 37.4 (9.0) (16-56) |
| SP-MS | 3 | | 48.7 (11) (36-56) |
| PP-MS | 6 | | 47.3 (8.3) (38-57) |
| NIND | 64 | 34/30 | 55.4 (17.6) (21-93) |
| OIND | 30 | 15/15 | 43.5 (15) (19-81) |

TABLE 2

Characteristics of patients used for affinity selections

| Subject | Gender (M/F) | Age (years) | Age start disease (years) | Disease duration (years) | Diagnosis | EDSS |
|---|---|---|---|---|---|---|
| 1 | F | 49 | 40 | 8 | RR-MS | 3, 5 |
| 2 | M | 42 | 34 | 8 | RR-MS | 1, 5 |
| 3 | F | 52 | 49 | 3 | RR-MS | 1, 5 |
| 4 | F | 41 | 38 | 3 | RR-MS | 3, 0 |
| 5 | F | 52 | 51 | 0.5 | RR-MS | 1, 0 |
| 6 | F | 48 | 46 | 0.6 | RR-MS | 1, 5 |
| 7 | F | 46 | 44 | 1 | RR-MS | 2, 5 |
| 8 | F | 43 | 35 | 7 | RR-MS | 1, 5 |
| 9 | F | 36 | 32 | 3 | RR-MS | 1, 5 |
| 10 | M | 31 | 27 | 4 | RR-MS | 0 |

TABLE 3

Sequence analysis of antigens retrieved by the selection of phage displayed MS cDNA expression library on MS patient CSF

| Name | GenBank No. | Vector pSP[a] | Identity | Translated amino acid sequence[b] | Size[c] | Comments |
|---|---|---|---|---|---|---|
| Antigens | | | | | | |
| UH-CSFP1.1 | NM014382 | B | HS ATP2C1, transcript variant 1 | ASSRGYEDLR | 12 | 3' UTR |
| UH-CSFP1.2 | NM199478 | B | PLP1, transcript variant 2 | LDNSYHDNPV | 23 | 3' UTR |
| UH-CSFP1.3 | BX509701.1 | A | HS DKFZp686A1481 | LRAPAGLGAA | 52 | Est |
| UH-CSFP1.4 | BC006427 | C | HS KIAA1279 | GARCINAEQP | 14 | out of frame |
| UH-CSFP1.5 | NM00729 | B | HS PACSIN2 | YSCLKLYSFA | 11 | 3' UTR |
| UH-CSFP1.6 | AC114947.2 | A | HS chromosome 5 clone CTD-2636A23 | EHATQNQVSV | 103 | |
| UH-CSFP1.7 | BC032450 | A | HS chromosome 10 ORF with retained intron | GTGSGQGEEA | 54 | |
| UH-CSFP1.8 | BC067756.1 | A | HS sperm associated antigen 16 | ADDNFSIPEG | 121 | in-frame |

[a] Reading frame of vector
[b] Translated amino acid sequence of the cDNA insert according to the reading frame of the vector: the first 10 aa of the fusion product are presented
[c] Size of protein product in amino acids fused to pVI coat protein, * stop codon

TABLE 4

Reactivity of panel of 8 phage clones on individual MS CSF used for the selection procedure

| | | CSF 1 | CSF 2 | CSF 3 | CSF 4 | CSF 5 | CSF 6 | CSF 7 | CSF 8 | CSF 9 | CSF 10 | | |
|---|---|---|---|---|---|---|---|---|---|---|---|---|---|
| Phage cDNA clones | UH-CSFP1.1 | − | − | − | + | − | − | + | + | − | − | 3/10 | Number of reactive CSF |
| | UH-CSFP1.2 | − | − | − | + | + | − | − | + | − | + | 4/10 | |
| | UH-CSFP1.3 | − | − | − | − | − | − | − | − | + | − | 1/10 | |
| | UH-CSFP1.4 | + | + | − | − | − | − | − | − | − | + | 3/10 | |
| | UH-CSFP1.5 | + | + | − | − | − | − | − | − | + | + | 4/10 | |
| | UH-CSFP1.6 | + | + | − | − | + | − | + | − | + | + | 6/10 | |
| | UH-CSFP1.7 | − | − | − | − | − | − | − | − | − | + | 1/10 | |
| | UH-CSFP1.8 | − | − | − | − | − | − | − | − | − | + | 1/10 | |
| Number of positive phage cDNA clones | | 3/8 | 3/8 | 0/8 | 2/8 | 2/8 | 0/8 | 2/8 | 2/8 | 3/8 | 6/8 | | |

+ positive ELISA signal at OD450 nm (>1.5x background)
− negative ELISA signal at OD450 nm (<1.5x background)

TABLE 5

ELISA screening of individual phage-cDNA clones on 167 different CSF

| Name | Selection[a] | Non-Selection[b] | Total | NIND[c] | OIND[d] | Total Controls |
|---|---|---|---|---|---|---|
| UH-CSFP1.1 | 3/10 | 3/63 | 6/73 | 3/64 | 1/30 | 4/94 |
| UH-CSFP1.2 | 4/10 | 6/63 | 10/73 | 1/64 | 0/30 | 1/94 |
| UH-CSFP1.3 | 1/10 | 4/63 | 5/73 | 0/64 | 1/30 | 1/94 |
| UH-CSFP1.4 | 3/10 | 1/63 | 4/73 | 0/64 | 0/30 | 0/94 |
| UH-CSFP1.5 | 4/10 | 2/63 | 6/73 | 0/64 | 0/30 | 0/94 |
| UH-CSFP1.6 | 6/10 | 4/63 | 10/73 | 0/64 | 0/30 | 0/94 |
| UH-CSFP1.7 | 1/10 | 4/63 | 5/73 | 0/64 | 0/30 | 0/94 |
| UH-CSFP1.8 | 1/10 | 13/63 | 14/73 | 7/64 | 0/30 | 7/94 |

[a] individual antigen reactive CSF from MS patients used in the selection procedure
[b] individual CSF from MS patients not used in the selection procedure
[c] NIND: hernia, epilepsy, dementia, headache, migraine, Alzheimer, hydrocephalus
[d] OIND: meningitis, polyneuropathy

TABLE 6

Comparison of antibody-positive and antibody-negative patients with established MS

| Characteristic | Antibody Positive (n = 33) | Antibody Negative (n = 40) | P |
|---|---|---|---|
| Age, mean ± SD years | 37.7 ± 8.9 | 39.4 ± 10.0 | NS |
| Disease duration, mean ± SD years | 3.6 ± 3.3 | 4.3 ± 5.2 | NS |
| Sex | | | |
| Male | 11 | 11 | |
| Female | 22 | 29 | |
| EDSS, gem ± SD | 2 ± 1 | 2 ± 1 | NS |

Age and disease duration were compared by t-test, and categorical variables were compared by chi-square testing with appropriate degrees of freedom.
NS = not significant

REFERENCES

1. Lucchinetti, C. F., Bruck, W., Rodriguez, M., and Lassmann, H. Distinct patterns of multiple sclerosis pathology indicates heterogeneity on pathogenesis. Brain Pathol., 6: 259-274, 1996.
2. Lucchinetti, C., Bruck, W., Parisi, J., Scheithauer, B., Rodriguez, M., and Lassmann, H. Heterogeneity of multiple sclerosis lesions: implications for the pathogenesis of demyelination. Ann. Neurol., 47: 707-717, 2000.
3. Genain, C. P., Cannella, B., Hauser, S. L., and Raine, C. S. Identification of autoantibodies associated with myelin damage in multiple sclerosis. Nat. Med., 5: 170-175, 1999.
4. Cross, A. H., Trotter, J. L., and Lyons, J. B cells and antibodies in CNS demyelinating disease. J. Neuroimmunol., 112: 1-14, 2001.
5. Qin, Y., Duquette, P., Zhang, Y., Talbot, P., Poole, R., and Antel, J. Clonal expansion and somatic hypermutation of V(H) genes of B cells from cerebrospinal fluid in multiple sclerosis. J. Clin. Invest, 102: 1045-1050, 1998.
6. Baranzini, S. E., Jeong, M. C., Butunoi, C., Murray, R. S., Bernard, C. C., and Oksenberg, J. R. B cell repertoire diversity and clonal expansion in multiple sclerosis brain lesions. J. Immunol., 163: 5133-5144, 1999.
7. Karni, A., Bakimer-Kleiner, R., Abramsky, O., and Ben Nun, A. Elevated levels of antibody to myelin oligodendrocyte glycoprotein is not specific for patients with multiple sclerosis. Arch. Neurol., 56: 311-315, 1999.
8. Moller, J. R., Johnson, D., Brady, R. O., Tourtellotte, W. W., and Quarles, R. H. Antibodies to myelin-associated glycoprotein (MAG) in the cerebrospinal fluid of multiple sclerosis patients. J. Neuroimmunol., 22: 55-61, 1989.
9. Vojdani, A., Vojdani, E., and Cooper, E. Antibodies to myelin basic protein, myelin oligodendrocytes peptides, alpha-beta-crystallin, lymphocyte activation and cytokine production in patients with multiple sclerosis. J. Intern. Med., 254: 363-374, 2003.
10. Lalive, P. H., Menge, T., Delarasse, C., Della, G. B., Pham-Dinh, D., Villoslada, P., von Budingen, H. C., and Genain, C. P. Antibodies to native myelin oligodendrocyte glycoprotein are serologic markers of early inflammation in multiple sclerosis. Proc. Natl. Acad. Sci. U.S.A, 103: 2280-2285, 2006.
11. O'Connor, K. C., Chitnis, T., Griffin, D. E., Piyasirisilp, S., Bar-Or, A., Khoury, S., Wucherpfennig, K. W., and Hafler, D. A. Myelin basic protein-reactive autoantibodies in the serum and cerebrospinal fluid of multiple sclerosis patients are characterized by low-affinity interactions. J. Neuroimmunol., 136: 140-148, 2003.
12. Almeras, L., Lefranc, D., Drobecq, H., de Seze, J., Dubucquoi, S., Vermersch, P., and Prin, L. New antigenic candidates in multiple sclerosis: identification by serological proteome analysis. Proteomics., 4: 2184-2194, 2004.
13. Kolln, J., Ren, H. M., Da, R. R., Zhang, Y., Spillner, E., Olek, M., Hermanowicz, N., Hilgenberg, L. G., Smith, M. A., Van Den, N. S., and Qin, Y. Triosephosphate isomerase- and glyceraldehyde-3-phosphate dehydrogenase-reactive autoantibodies in the cerebrospinal fluid of patients with multiple sclerosis. J. Immunol., 177: 5652-5658, 2006.
14. Poser, C. M., Paty, D. W., Scheinberg, L., McDonald, W. I., Davis, F. A., Ebers, G. C., Johnson, K. P., Sibley, W. A., Silberberg, D. H., and Tourtellotte, W. W. New diagnostic criteria for multiple sclerosis: guidelines for research protocols. Ann. Neurol., 13: 227-231, 1983.
15. Somers, V., Govarts, C., Hellings, N., Hupperts, R., and Stinissen, P. Profiling the autoantibody repertoire by serological antigen selection. J. Autoimmun., 25: 223-228, 2005.
16. Marks, J. D., Hoogenboom, H. R., Bonnert, T. P., McCafferty, J., Griffiths, A. D., and Winter, G. By-passing immunization. Human antibodies from V-gene libraries displayed on phage. J Mol Biol, 222: 581-97, 1991.
17. Somers, V. A., Brandwijk, R. J., Joosten, B., Moerkerk, P. T., Arends, J. W., Menheere, P., Pieterse, W. O., Claessen, A., Scheper, R. J., Hoogenboom, H. R., and Hufton, S. E. A panel of candidate tumor antigens in colorectal cancer revealed by the serological selection of a phage displayed cDNA expression library. J. Immunol., 169: 2772-2780, 2002.
18. Cortese, I., Tafi, R., Grimaldi, L. M., Martino, G., Nicosia, A., and Cortese, R. Identification of peptides specific for cerebrospinal fluid antibodies in multiple sclerosis by using phage libraries. Proc. Natl. Acad. Sci. U.S.A, 93: 11063-11067, 1996.
19. Archelos, J. J., Trotter, J., Previtali, S., Weissbrich, B., Toyka, K. V., and Hartung, H. P. Isolation and characterization of an oligodendrocyte precursor-derived B-cell epitope in multiple sclerosis. Ann. Neurol., 43: 15-24, 1998.
20. Owens, G. P., Burgoon, M. P., Devlin, M. E., and Gilden, D. H. Strategies to identify sequences or antigens unique to multiple sclerosis. Mult. Scler., 2: 184-194, 1996.
21. Cortese, I., Capone, S., Luchetti, S., Grimaldi, L. M., Nicosia, A., and Cortese, R. CSF-enriched antibodies do not share specificities among MS patients. Mult. Scler., 4: 118-123, 1998.
22. Becker, K. G., Mattson, D. H., Powers, J. M., Gado, A. M., and Biddison, W. E. Analysis of a sequenced cDNA library from multiple sclerosis lesions. J. Neuroimmunol., 77: 27-38, 1997.
23. Robinson, W. H., Fontoura, P., Lee, B. J., de Vegvar, H. E., Tom, J., Pedotti, R., DiGennaro, C. D., Mitchell, D. J., Fong, D., Ho, P. P., Ruiz, P. J., Maverakis, E., Stevens, D. B., Bernard, C. C., Martin, R., Kuchroo, V. K., van Noort, J. M., Genain, C. P., Amor, S., Olsson, T., Utz, P. J., Garren, H., and Steinman, L. Protein microarrays guide tolerizing DNA vaccine treatment of autoimmune encephalomyelitis. Nat. Biotechnol., 21: 1033-1039, 2003.
24. Neer, E. J., Schmidt, C. J., Nambudripad, R., and Smith, T. F. The ancient regulatory-protein family of WD-repeat proteins. Nature, 371: 297-300, 1994.
25. Smith, T. F., Gaitatzes, C., Saxena, K., and Neer, E. J. The WD repeat: a common architecture for diverse functions. Trends Biochem. Sci., 24: 181-185, 1999.

26. Smith, E. F. and Lefebvre, P. A. PF20 gene product contains WD repeats and localizes to the intermicrotubule bridges in *Chlamydomonas flagella*. Mol. Biol. Cell, 8: 455-467, 1997.
27. Strausberg, R. L., Feingold, E. A., Grouse, L. H., Derge, J. G., Klausner, R. D., Collins, F. S., Wagner, L., Shenmen, C. M., Schuler, G. D., Altschul, S. F., Zeeberg, B., Buetow, K. H., Schaefer, C. F., Bhat, N. K., Hopkins, R. F., Jordan, H., Moore, T., Max, S. I., Wang, J., Hsieh, F., Diatchenko, L., Marusina, K., Farmer, A. A., Rubin, G. M., Hong, L., Stapleton, M., Soares, M. B., Bonaldo, M. F., Casavant, T. L., Scheetz, T. E., Brownstein, M. J., Usdin, T. B., Toshiyuki, S., Carninci, P., Prange, C., Raha, S. S., Loquellano, N. A., Peters, G. J., Abramson, R. D., Mullahy, S. J., Bosak, S. A., McEwan, P. J., McKernan, K. J., Malek, J. A., Gunaratne, P. H., Richards, S., Worley, K. C., Hale, S., Garcia, A. M., Gay, L. J., Hulyk, S. W., Villalon, D. K., Muzny, D. M., Sodergren, E. J., Lu, X., Gibbs, R. A., Fahey, J., Helton, E., Ketteman, M., Madan, A., Rodrigues, S., Sanchez, A., Whiting, M., Madan, A., Young, A. C., Shevchenko, Y., Bouffard, G. G., Blakesley, R. W., Touchman, J. W., Green, E. D., Dickson, M. C., Rodriguez, A. C., Grimwood, J., Schmutz, J., Myers, R. M., Butterfield, Y. S., Krzywinski, M. I., Skalska, U., Smailus, D. E., Schnerch, A., Schein, J. E., Jones, S. J., and Marra, M. A. Generation and initial analysis of more than 15,000 full-length human and mouse cDNA sequences. Proc. Natl. Acad. Sci. U.S.A, 99: 16899-16903, 2002.
28. Ota, T., Suzuki, Y., Nishikawa, T., Otsuki, T., Sugiyama, T., Irie, R., Wakamatsu, A., Hayashi, K., Sato, H., Nagai, K., Kimura, K., Makita, H., Sekine, M., Obayashi, M., Nishi, T., Shibahara, T., Tanaka, T., Ishii, S., Yamamoto, J., Saito, K., Kawai, Y., Isono, Y., Nakamura, Y., Nagahari, K., Murakami, K., Yasuda, T., Iwayanagi, T., Wagatsuma, M., Shiratori, A., Sudo, H., Hosoiri, T., Kaku, Y., Kodaira, H., Kondo, H., Sugawara, M., Takahashi, M., Kanda, K., Yokoi, T., Furuya, T., Kikkawa, E., Omura, Y., Abe, K., Kamihara, K., Katsuta, N., Sato, K., Tanikawa, M., Yamazaki, M., Ninomiya, K., Ishibashi, T., Yamashita, H., Murakawa, K., Fujimori, K., Tanai, H., Kimata, M., Watanabe, M., Hiraoka, S., Chiba, Y., Ishida, S., Ono, Y., Takiguchi, S., Watanabe, S., Yosida, M., Hotuta, T., Kusano, J., Kanehori, K., Takahashi-Fujii, A., Hara, H., Tanase, T. O., Nomura, Y., Togiya, S., Komai, F., Hara, R., Takeuchi, K., Arita, M., Imose, N., Musashino, K., Yuuki, H., Oshima, A., Sasaki, N., Aotsuka, S., Yoshikawa, Y., Matsunawa, H., Ichihara, T., Shiohata, N., Sano, S., Moriya, S., Momiyama, H., Satoh, N., Takami, S., Terashima, Y., Suzuki, O., Nakagawa, S., Senoh, A., Mizoguchi, H., Goto, Y., Shimizu, F., Wakebe, H., Hishigaki, H., Watanabe, T., Sugiyama, A., Takemoto, M., Kawakami, B., Yamazaki, M., Watanabe, K., Kumagai, A., Itakura, S., Fukuzumi, Y., Fujimori, Y., Komiyama, M., Tashiro, H., Tanigami, A., Fujiwara, T., Ono, T., Yamada, K., Fujii, Y., Ozaki, K., Hirao, M., Ohmori, Y., Kawabata, A., Hikiji, T., Kobatake, N., Inagaki, H., Ikema, Y., Okamoto, S., Okitani, R., Kawakami, T., Noguchi, S., Itoh, T., Shigeta, K., Senba, T., Matsumura, K., Nakajima, Y., Mizuno, T., Morinaga, M., Sasaki, M., Togashi, T., Oyama, M., Hata, H., Watanabe, M., Komatsu, T., Mizushima-Sugano, J., Satoh, T., Shirai, Y., Takahashi, Y., Nakagawa, K., Okumura, K., Nagase, T., Nomura, N., Kikuchi, H., Masuho, Y., Yamashita, R., Nakai, K., Yada, T., Nakamura, Y., Ohara, O., Isogai, T., and Sugano, S. Complete sequencing and characterization of 21,243 full-length human cDNAs. Nat. Genet., 36: 40-45, 2004.
29. Ng, B., Yang, F., Huston, D. P., Yan, Y., Yang, Y., Xiong, Z., Peterson, L. E., Wang, H., and Yang, X. F. Increased non-canonical splicing of autoantigen transcripts provides the structural basis for expression of untolerized epitopes. J. Allergy Clin. Immunol., 114: 1463-1470, 2004.
30. Yeo, G., Holste, D., Kreiman, G., and Burge, C. B. Variation in alternative splicing across human tissues. Genome Biol., 5: R74, 2004.
31. Larsen, J. E., Lund, O., and Nielsen, M. Improved method for predicting linear B-cell epitopes. Immunome. Res., 2: 2, 2006.
32. Cepok, S., Zhou, D., Srivastava, R., Nessler, S., Stei, S., Bussow, K., Sommer, N., and Hemmer, B. Identification of Epstein-Barr virus proteins as putative targets of the immune response in multiple sclerosis. J. Clin. Invest, 115: 1352-1360, 2005.
33. Wang, X., Yu, J., Sreekumar, A., Varambally, S., Shen, R., Giacherio, D., Mehra, R., Montie, J. E., Pienta, K. J., Sanda, M. G., Kantoff, P. W., Rubin, M. A., Wei, J. T., Ghosh, D., and Chinnaiyan, A. M. Autoantibody signatures in prostate cancer. N. Engl. J. Med., 353: 1224-1235, 2005.
34. Keegan, M., Konig, F., McClelland, R., Bruck, W., Morales, Y., Bitsch, A., Panitch, H., Lassmann, H., Weinshenker, B., Rodriguez, M., Parisi, J., and Lucchinetti, C. F. Relation between humoral pathological changes in multiple sclerosis and response to therapeutic plasma exchange. Lancet, 366: 579-582, 2005.
35. Stuve, O., Cepok, S., Elias, B., Saleh, A., Hartung, H. P., Hemmer, B., and Kieseier, B. C. Clinical stabilization and effective B-lymphocyte depletion in the cerebrospinal fluid and peripheral blood of a patient with fulminant relapsing-remitting multiple sclerosis. Arch. Neurol, 62: 1620-1623, 2005.

The invention claimed is:

1. A composition comprising at least two different polypeptides, the composition comprising SEQ ID NOS:1 and 8.

2. A method of detecting the presence and/or quantity of specific antibodies to at least one polypeptide comprising a sequence represented by SEQ ID NO:1 and/or SEQ ID NO:8, the method comprising contacting cerebrospinal fluid of a mammal with the composition of claim 1, and detecting the presence and/or measuring the quantity of the specific antibodies bound to the composition.

3. The method according to claim 2, wherein the mammal is a human.

4. The method according to claim 2, wherein the detecting and/or measuring comprises utilizing an immune-enzymatic process selected from the group consisting of an enzyme-linked immunosorbant assay (ELISA), an immunofluorescent technique, a radioimmunological assay (RIA), immunoblotting and a LINE blot.

5. The method according to claim 2, wherein the presence and/or quantity of at least one specific antibody is indicative for multiple sclerosis.

6. A diagnostic kit for the detection of multiple sclerosis, the diagnostic kit comprising the composition of claim 1, reagents for making a medium appropriate for an immunological reaction to occur, and reagents enabling detection of the antigen/antibody complex, which has been produced by the immunological reaction between antibodies from a cerebrospinal fluid of a human and the composition of claim 1.

7. The composition of claim 1, wherein one or more of the polypeptides are bound to a solid support.

8. The composition of claim 7, wherein the composition forms part of an ELISA.

9. The composition of claim 1, wherein the polypeptides are labeled.

10. The composition of claim 9, wherein the label comprises an enzymatic, fluorescent, biotin, or radioactive label.

* * * * *

SEQUENCE LISTING

<160> NUMBER OF SEQ ID NOS: 24

<210> SEQ ID NO 1
<211> LENGTH: 12
<212> TYPE: PRT
<213> ORGANISM: Homo sapiens

<400> SEQUENCE: 1

Ala Ser Ser Arg Gly Tyr Glu Asp Leu Arg Thr Phe
1               5                   10

<210> SEQ ID NO 2
<211> LENGTH: 23

<212> TYPE: PRT
<213> ORGANISM: Homo sapiens

<400> SEQUENCE: 2

Leu Asp Asn Ser Tyr His Asp Asn Pro Val Ser Lys Glu Leu Arg
1               5                   10                  15

Ile Glu Gly Asn Gln Leu Thr
            20

<210> SEQ ID NO 3
<211> LENGTH: 53
<212> TYPE: PRT
<213> ORGANISM: Homo sapiens

<400> SEQUENCE: 3

Leu Arg Ala Pro Ala Gly Leu Gly Ala Ala Cys Asp Asn Trp Cys Ile
1               5                   10                  15

Trp Gln Glu Gln Gln Leu Pro Leu Gly Ala Thr Ala Gly Ala Ala Asn
            20                  25                  30

Gln Arg Asn Thr Asp Thr Pro His Arg Ala Thr Ala Ser Leu Gly Ala
        35                  40                  45

Trp Ser Pro Pro Arg
    50

<210> SEQ ID NO 4
<211> LENGTH: 14
<212> TYPE: PRT
<213> ORGANISM: Homo sapiens

<400> SEQUENCE: 4

Gly Ala Arg Cys Ile Asn Ala Glu Gln Pro Cys Gln Ser Pro
1               5                   10

<210> SEQ ID NO 5
<211> LENGTH: 11
<212> TYPE: PRT
<213> ORGANISM: Homo sapiens

<400> SEQUENCE: 5

Tyr Ser Cys Leu Lys Leu Tyr Ser Phe Ala Asn
1               5                   10

<210> SEQ ID NO 6
<211> LENGTH: 104
<212> TYPE: PRT
<213> ORGANISM: Homo sapiens

<400> SEQUENCE: 6

Glu His Ala Thr Gln Asn Gln Val Ser Val Ser Asp Lys Gln Val Lys
1               5                   10                  15

Gly Leu Leu Ile Leu Lys Thr Glu Lys Gln Lys Arg Lys Gly Lys Lys
            20                  25                  30

Ser Ala Ser Arg Ile Ala Ile Gly Gly Ser Phe Ala Gly Ala Asp Cys
        35                  40                  45

Gln Leu Arg Leu Phe Lys Pro Gln Ser Lys His Ser Ala Pro Ala Pro
    50                  55                  60

Leu Glu Leu Pro Ser His Arg Ser Val Leu Pro Pro Ala Arg Gly Gly
65                  70                  75                  80

Leu Ala Ala Ala Asp Thr Ser Glu Pro Phe Phe His Ser Arg Ser Pro
                85                  90                  95

Ser Gly Pro Thr Leu Ile Tyr Gln
            100

<210> SEQ ID NO 7
<211> LENGTH: 55
<212> TYPE: PRT
<213> ORGANISM: Homo sapiens

<400> SEQUENCE: 7

Gly Thr Gly Ser Gly Gln Gly Glu Glu Ala Ala Tyr Leu Thr Asn Gln
1               5                   10                  15

Pro Leu Cys Gly Pro Pro Ala Ser Trp Leu Gly Gly Arg Ala Leu Asn
            20                  25                  30

Gln Gln Gly Pro Arg Arg Glu Glu Val Gly Gln Ser Leu Ala Ser
        35                  40                  45

Pro Leu Gly Ser Phe Ala Ile
    50                  55

<210> SEQ ID NO 8
<211> LENGTH: 121
<212> TYPE: PRT
<213> ORGANISM: Homo sapiens

<400> SEQUENCE: 8

Ala Asp Asp Asn Phe Ser Ile Pro Glu Gly Glu Glu Asp Leu Ala Lys
1               5                   10                  15

Ala Ile Gln Met Ala Gln Glu Gln Ala Thr Asp Thr Glu Ile Leu Glu
            20                  25                  30

Arg Lys Thr Val Leu Pro Ser Lys His Ala Val Pro Val Ile Glu
            35                  40                  45

Asp Phe Leu Cys Asn Phe Leu Ile Lys Met Gly Met Thr Arg Thr Leu
50                  55                  60

Asp Cys Phe Gln Ser Glu Trp Tyr Glu Leu Ile Gln Lys Gly Val Thr
65                  70                  75                  80

Glu Leu Arg Thr Val Gly Asn Val Pro Asp Val Tyr Thr Gln Ile Met
                85                  90                  95

Leu Leu Glu Asn Glu Asn Lys Asn Leu Lys Lys Asp Leu Lys His Tyr
            100                 105                 110

Lys Gln Ala Ala Glu Tyr Val Ile Phe
        115                 120

<210> SEQ ID NO 9
<211> LENGTH: 603
<212> TYPE: DNA
<213> ORGANISM: Homo sapiens

<400> SEQUENCE: 9
ggcaagttca agaggatatg aagatttgag aacttttttaa ctattcattg actaaaaatg     60
aacattaatg ttaaagactt aagactttaa cctgctggca gtcccaaatg aaattatgca    120
actttgatat catattcctt gatttaaatt ggcttttgtg attgagtgaa acttataaa     180 gcatatggtc agttatttaa ttaaaaaggc aaaacctgaa ccaccttctg cacttaaaga    240
agtctaacag tacaaataca ctatctatct tagatagata tatttttttt tattttttaaa   300 tattgtacta tttatggtgg tggggctttc ttactaatac acaaataaat ttaatcattt    360
caaaggcatt ctatttggtt tagaagttga ttcccaggag tgccatattt cagctactgt    420
atttcctttt tcttgtaatg taagcagctc agataccatg tgctatcatt tttgtatcaa    480

```
gttttttgca caggatgtga ccactgtcag atcactgttc ttttctttct ttttgtgatt      540
gaaaagccta tactacaatt tgaagtaaat ttttgttttt cttaaaaaaa aaaaaaaaa      600 aaa                                                                   603

<210> SEQ ID NO 10
<211> LENGTH: 783
<212> TYPE: DNA
<213> ORGANISM: Homo sapiens

<400> SEQUENCE: 10
ccttgataac agctaccatg acaaccctgt ggtttccaag gagctgagaa tagaaggaaa       60
ctagcttaca tgagaacaga ctggcctgag gagcagcagt tgctggtggc taatggtgta     120
acctgagatg cccctctggt agacacagga tagataactc tttggatagc atgtcttttt     180
ttctgttaat tagttgtgta ctctggcctc tgtcatatct tcacaatggt gctcatttca     240 tggggtatt atccattcag tcatcgtagg tgatttgaag gtcttgattt gttttagaat      300
gatgcacatt tcatgtattc cagtttgttt attacttatt tggggttgca tcagaaatgt     360
ctggagaata attctttgat tatgactgtt ttttaaacta ggaaaattgg acattaagca     420
tcacaaatga tattaaaaat tggctagttg aatctattgg gattttctac aagtattctg     480
cctttgcaga aacagatttg gtgaatttga atctcaattt gagtaatctg atcgttcttt     540
ctagctaatg gaaaatgatt ttacttagca atgttatctt ggtgtgttaa gagttaggtt     600
taacataaag gttattttct cctgatatag atcacataac agaatgcacc agtcatcagc     660
tattcagttg gtaagcttcc aggaaaaagg acaggcagaa agagtttgag acctgaatag     720
ctcccagatt tcagtctttt cctgtttttg ttaactttgg gttaaaaaaa aaaaaaaaa     780 aaa                                                                   783

<210> SEQ ID NO 11
<211> LENGTH: 539
<212> TYPE: DNA
<213> ORGANISM: Homo sapiens

<400> SEQUENCE: 11
aattctcagg gccccgcag gcctgggagc ggcctgtgat aactggtgta tctggcagga       60
gtagcagctg cccttggcg cgactgctgg agccgcgaac tagagaaaca cagacacgcc      120
tcatagagca acggcgtctc tcggagcgtg gagcccgcca aggtaactcc gggaattgag     180
tggagtggag gctgcactga ggcccccttc tggctcctct ctggtcgaaa aggctccccc     240
gctagagaga gccctgctgc ttttggaagc cttcaggtgt tagttgcttt gcaccgaagc     300
tgctgactgc tggggttctg cgccgattgc caggctcaag tttatttggg gggctgctga     360
gcagactttg cccttctgtg ctgttatcag cttctgtcgc tgtccgtcca cgcccgctat     420
atccatccac tctccgttct gtctccagca ggcaactccc cctaccctgc cccatttttct    480 gggtcatagg ggtatttgaa ataaaccttt aagggaaaag caaaaaaaaa aaaaaaaaa      539

<210> SEQ ID NO 12
<211> LENGTH: 1119
<212> TYPE: DNA
<213> ORGANISM: Homo sapiens

<400> SEQUENCE: 12
ggtgcaagat gcataaacgc agaatagcca tgctagagcc cctaactgta gacctgaatc       60
cacagtatta tctgttggtc aacagacaga tccagtttga aattgcacat gcttactatg      120
```

| | |
|---|---|
| atatgatgga tttgaaggtt gccattgctg acaggctaag ggatcctgat tcacacattg | 180 |
| taaaaaaaat aaataatctt aataagtcag cactgaagta ctaccagctc ttcttagact | 240 |
| ccctgagaga cccaaataaa gtattccctg agcatatagg ggaagatgtt cttcgccctg | 300 |
| ccatgttagc taagtttcga gttgcccgtc tctatggcaa aatcattact gcagatccca | 360 |
| agaaagagct ggaaaatttg gcaacatcat tggaacatta caaatttatt gttgattact | 420 |
| gtgaaaagca tcctgaggcc gcccaggaaa tagaagttga gctagaactt agtaaagaga | 480 |
| tggttagtct tctcccaaca aaaatggaga gattcagaac caagatggcc ctgacttaat | 540 |
| ccttgttttt aaagaaagga aatgtgcaat attgaagtga tctttttccc tagtcagaca | 600 |
| ggcccaattc cattgtgatg tttacccttta tagccaggtg agtgcagttt gaacttgaga | 660 |
| tacagtcaac tgagtgtttg ctaggatcct aaggaacata aagttaatta aaaacttaca | 720 |
| cctaattatg taaattgcct tgttaaagac atgtgatttg tatttagat gcttgtttcc | 780 |
| tattaaaata cagacatttc taccctcagt ttctaaatgt agactatttg ttggctagta | 840 |
| cttgatagat tccttgtaag aaaaaatgct gggtaatgta cctggtaaca agcctgttaa | 900 |
| tatattaaga ttgaaaaagt aacttctata gttactcctt ctaaaatatt tgacttccta | 960 |
| aattcccccc acccaaaatc tttcccttttt gaaaatacta aaaactaagt tatgttatta | 1020 |
| taaagtgtaa aatggtttgt cttaattata ggagaaaaag gccttgttag aaataaaata | 1080 |
| aactgactta tttcactaat gaaaaaaaaa aaaaaaaaa | 1119 |

```
<210> SEQ ID NO 13
<211> LENGTH: 864
<212> TYPE: DNA
<213> ORGANISM: Homo sapiens

<400> SEQUENCE: 13
```

| | |
|---|---|
| ctattcttgc ttaaaactgt actcttttgc aaattaacaa ttttatcact gattcagagt | 60 |
| taaaagaag actaacttttt caagcaaatg catctgtaaa gatgctttag attagactgt | 120 |
| catgtctcag tgtctatctg tatatattat ttgatattca gagaatctaa agcactcgtc | 180 |
| tactgttta atgagattta acagctttta acagtgagtt tcgtttgtaa actgcttgaa | 240 |
| gtctgtggca ttcaggcaca cgtctggctg gccggctggg tctcctcccg ggctcagtgg | 300 |
| gcctggggcc tctctgacgt ggtgcctgct ggagggaggc tcgtcgtcac cagctgactg | 360 |
| ctggtccggc ttctgaccgg cctttgtcct ggctccgtag cagaacactg taaaagtgcc | 420 |
| cgcgtctttg cagtagttgc agatttcagt cgtcgtgtta cttgtgcaca aacagaagct | 480 |
| gggtcttacc cgcagcacga gtgtctcggg ctgcccggag tcgcccggga gcaggtgctg | 540 |
| cagccagagt tacgcggggg ccacgcgggc cggcgggggt ggggggaacg tgggggaacc | 600 |
| tgtgtttcac gtgactcagc agtgcccgcc gccgtcacca gctatgcatt cactccgttt | 660 |
| ccagtgagca gatgtcttgc ttggaaagtg gacctgtgtc tgtgtctgtc ctgagaactt | 720 |
| accagcagaa atcctcattt ctgtgctacg gatttaccaa aaattgtcaa gtcttttttca | 780 |
| gtttaacagt tcctttacat gtgtagtatt tgaggaaaaa aatcaataaa cagttgatct | 840 |
| cgtgcataaa aaaaaaaaaa aaaa | 864 |

```
<210> SEQ ID NO 14
<211> LENGTH: 790
<212> TYPE: DNA
<213> ORGANISM: Homo sapiens
```

<400> SEQUENCE: 14

```
aacatgctac acaaaaccag gtttctgttt cagataaata ggtgaaggga ctcttaatcc    60
taaagactga aaagtagaaa agaaagggga agaagagtgc ctcaaggatt gccattggag   120
gttcttttgc tggggctgat tgccagctga gattattcaa gccccagagc aaacattctg   180
ctcctgctcc cttagagctg ccctcccacc gctcagtatt gcctcctgcg aggggcgggc   240
tggctgccgc agacaccagt gaacccttt tccattccag aagtcccagt ggacctactt    300
taatatacca ataacactcc tatttaaac tagctgtatc cattttcgtt ttaatagtcc    360
cagtgctaaa gttttcaaa gcagttattt tgtaagtagg tcaaacaggt actttgggat    420
cctgttctgt ctgtttgctt gccaggtaac ctctttgtta tctaattcaa agtctggtac   480
agtttgaacc aaaacaaaaa aggaatgatg tttcactttg gagtcaagat tcattcattt   540
tctaacatta atcattttcg ttatacagta agtctatatt catgataaaa aatagaaaat   600
atgaataagc aaaactaaat tgaaggaaa accatctgtg atctgccaat tagaaaatct    660
ctattctaaa cattttggta aatatgctac cagatttta tctatgcaaa tgtgtatctg    720
tatttttcct cacttgtata gtggacatct tttcatatta ataaataagt tagcatcaaa   780
aaaaaaaaaa                                                          790
```

<210> SEQ ID NO 15
<211> LENGTH: 681
<212> TYPE: DNA
<213> ORGANISM: Homo sapiens

<400> SEQUENCE: 15

```
ggacagggag tgggcaaggg gaagaagcag cttatttgac taaccagccc ctctgtggtc    60
caccagcgtc ttggcttggt gggagggctc tcaatcagca gggccccagg agggaagaag   120
aagtggggca aagcctggcc tcgccgctcg ggagctttgc catctgagcc acgcctcctc   180
caggccatgc tccttgaact tggaaatgtc aaccggagcc cttacaccag ccctccagca   240
tctaatagac ttgaatctac tctaaacgaa tatttaatcc aacctcacta cattgtagct   300
cagtccaacg actaaccctg aaatgggggt gttccagcct tcagcgagat ggccaagcgg   360
tccctgggg gctgtggcag cgggcttatc cttctctgtt gccaaccttg ccgtccgacc    420
tcctccgccc ccatgcggtg accccgtccg tgtctgtgtc tgtccatacg tgtgagtcca   480
gctaaaaaga caaaacagaa cccgtgggcc cagctcggaa ggtgcgtgga aaggctccg    540
acgtctccga agtgcagccc ttgggatggc attccgttgt gtgccttatt cctggagaat   600
ctgtatacgg ctcgcctata gaaatatagc ctcttcatgc tgtattaaaa ggactttaa    660
aagcaaaaaa aaaaaaaaaa a                                             681
```

<210> SEQ ID NO 16
<211> LENGTH: 970
<212> TYPE: DNA
<213> ORGANISM: Homo sapiens

<400> SEQUENCE: 16

```
cagatgacaa ttttagcatc ccagaaggtg aagaagatct ggcaaaagca attcagatgg    60
cccaagaaca ggctacagat actgaaattt tggaacggaa aacagttctt ccttcaaagc   120
atgcagtacc tgaagtaata gaagactttc tctgcaattt cttgatcaaa atgggaatga   180
ccagaactct tgattgcttt cagtctgaat ggtatgagtt aatacagaaa ggagtgactg   240
aacttagaac tgttgggaat gttccagatg tctacaccca gattatgctg ttggaaaatg   300
```

```
agaacaaaaa tttaaagaaa gatttgaagc actacaaaca agcagctgag tatgttattt    360
tttaaatgac attttcttct ttttcttttg gactaaataa aagagttgag tgaagctgat    420
atatgtaata taccagagcc ttaattttg aaaactgaat ttttctagtt gtaaagaatg    480
tgagaggctt cattagcaaa ttaattaaac agatgatcag aactatcaca attataactt    540
accaacaaga agggaatgca ggtagttgtt taggagatgg tacatttttt atataacatt    600
cacttccttg tgtatttgat agtcttttca tggtttataa catttctcc tgtaaagata     660 ggctaatttc tgaaataata attaaattta tagaaagccg agaggaaatt gctagtttat    720
tcctggtaga ggaatttctg tatttgaaaa ttctccagaa ggaataatat aaactgtgga    780
ctttgggtga taatgatatg taggttcgtc agttgttaac aaatgtatcc ctctgttggg    840
ggctattgat aatggggaag gctgtgcatg tgtgggagta ggaggtgtat gggacatctc    900
tgtaccttct aatcaatttt gctatgaact taaaactgct ctaaaaataa aaaaaaaaa     960 aaaaaaaaaa                                                           970
```

<210> SEQ ID NO 17
<211> LENGTH: 10
<212> TYPE: PRT
<213> ORGANISM: Homo sapiens

<400> SEQUENCE: 17

Ala Ser Ser Arg Gly Tyr Glu Asp Leu Arg
1               5                   10

<210> SEQ ID NO 18
<211> LENGTH: 10
<212> TYPE: PRT
<213> ORGANISM: Homo sapiens

<400> SEQUENCE: 18

Leu Asp Asn Ser Tyr His Asp Asn Pro Val
1               5                   10

<210> SEQ ID NO 19
<211> LENGTH: 10
<212> TYPE: PRT
<213> ORGANISM: Homo sapiens

<400> SEQUENCE: 19

Leu Arg Ala Pro Ala Gly Leu Gly Ala Ala
1               5                   10

<210> SEQ ID NO 20
<211> LENGTH: 10
<212> TYPE: PRT
<213> ORGANISM: Homo sapiens

<400> SEQUENCE: 20

Gly Ala Arg Cys Ile Asn Ala Glu Gln Pro
1               5                   10

<210> SEQ ID NO 21
<211> LENGTH: 10
<212> TYPE: PRT
<213> ORGANISM: Homo sapiens

<400> SEQUENCE: 21

Tyr Ser Cys Leu Lys Leu Tyr Ser Phe Ala
1               5                   10

```
<210> SEQ ID NO 22
<211> LENGTH: 10
<212> TYPE: PRT
<213> ORGANISM: Homo sapiens

<400> SEQUENCE: 22

Glu His Ala Thr Gln Asn Gln Val Ser Val
1               5                   10

<210> SEQ ID NO 23
<211> LENGTH: 10
<212> TYPE: PRT
<213> ORGANISM: Homo sapiens

<400> SEQUENCE: 23

Gly Thr Gly Ser Gly Gln Gly Glu Glu Ala
1               5                   10

<210> SEQ ID NO 24
<211> LENGTH: 10
<212> TYPE: PRT
<213> ORGANISM: Homo sapiens

<400> SEQUENCE: 24

Ala Asp Asp Asn Phe Ser Ile Pro Glu Gly
1               5                   10
```